United States Patent [19]

Collington et al.

[11] Patent Number: 4,613,597
[45] Date of Patent: Sep. 23, 1986

[54] AMINOCYCLOPENTANES AND THEIR PREPARATION AND PHARMACEUTICAL FORMULATION

[75] Inventors: Eric W. Collington, Welwyn; Peter Hallett; Christopher J. Wallis, both of Royston; Norman F. Hayes, Hitchin, all of England

[73] Assignee: Glaxo Group Limited, London, England

[21] Appl. No.: 647,537

[22] Filed: Sep. 5, 1984

[30] Foreign Application Priority Data

Sep. 6, 1983 [GB] United Kingdom ............. 8323830
Jun. 6, 1984 [GB] United Kingdom ............. 8414676

[51] Int. Cl.$^4$ ............... A61K 31/55; C07D 295/08; C07D 295/10
[52] U.S. Cl. ................................ 514/211; 540/544; 514/212; 514/222; 514/234; 514/236; 514/238; 514/255; 514/317; 514/326; 514/438; 514/444; 544/59; 544/60; 544/171; 544/174; 544/379; 544/398; 544/399; 544/400; 544/401; 546/207; 546/213; 546/233; 546/234; 546/237; 546/238; 546/239; 546/240; 548/517; 548/527; 548/575; 549/59; 540/484
[58] Field of Search ............ 546/213, 207, 233, 234, 546/236, 237, 238, 239, 240; 548/517, 527, 575; 544/59, 60, 146, 162; 260/239 BF; 514/211, 212, 255, 222, 238, 236, 234, 326, 331, 317, 444, 438

[56] References Cited

U.S. PATENT DOCUMENTS 4,447,428 5/1984 Collington et al. ............. 546/213
4,482,549 11/1984 Collington et al. ............. 546/213

*Primary Examiner*—Robert T. Bond
*Attorney, Agent, or Firm*—Bernard, Rothwell & Brown

[57] ABSTRACT

Compounds are described of the formulae (1a) and 1b)

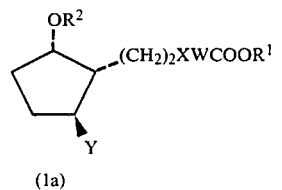 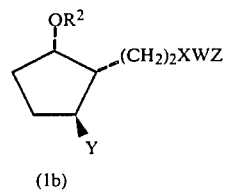

(1a) (1b)

in which:
$R^1$ is -H, $C_{1-6}$ alkyl or $C_{7-10}$ aralkyl,
W is $C_{1-7}$ alkylene
X is cis or trans —CH=CH—,
Y is a saturated heterocyclic amino group having 5-8 ring members,
$R^2$ is (i) substituted or unsubstituted phenylalkyl, thienylalkyl or naphthylalkyl or (ii) cinnamyl, and Z is —CH$_2$OH, —CHO or —CONHR$^4$ where $R^4$ is —H or methyl,
and their salts and solvates.

These compounds inhibit blood platelet aggregation, bronchoconstriction and vasoconstriction, and may be formulated for use as antithrombotic and antiasthmatic agents.

20 Claims, No Drawings

AMINOCYCLOPENTANES AND THEIR PREPARATION AND PHARMACEUTICAL FORMULATION

The endoperoxides prostaglandins $G_2$ and $H_2$ and thromboxane $A_2$ are naturally occurring reactive metabolites of arachidonic acid in human platelets. They are not only potent aggregatory agents but are also constrictors of vascular and bronchial smooth muscle, and therefore substances which antagonise their effects are of considerable interest in human medicine.

Our U.K. Patent Specification No. 2028805A describes a novel class of aminocyclopentane derivatives, represented here by the partial formula:

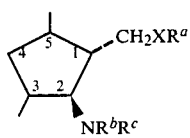

The compounds of Specification No. 2028805A inhibit blood platelet aggregation and bronchoconstriction. A very broad range of compounds is described, one of the principal characteristics of which is an amino substituent —$NR^bR^c$ at the 2-position. This may be an acyclic or heterocyclic group of many types. The substituent —$CH_2XR^a$ at the 1-position can be varied, and includes both saturated and unsaturated structures in which X is either —$CH_2CH_2$— or —CH=CH— and $R^a$ is an alkyl chain of variable length, terminally substituted by a carboxylic acid or ester function. As well as the possible variation in —$NR^bR^c$ and —$CH_2XR^a$, the compounds can have any one of eight different basic ring structures depending on the presence of an oxa function at the 3- and/or 5-positions and the presence or absence of a double bond at the 4,5- or 3,4- positions. The oxa function on the ring may be chosen from a wide range of possibilities, for example hydroxy, oxo, ether and ester groups.

Specification No. 2028805A thus embraces many different general possibilities and a large number of individual compounds is exemplified. Nearly all of these have a ring structure which has oxa functions at both the 3- and 5-positions, the remainder being concerned with the other ring structures described. In general however a preference clearly emerges for compounds with 3- and 5- oxa functions. The usefulness of ring structures of this type is further emphasised in U.K. Patent Specifications Nos. 2070591A, 2075503A, 2079281A, 2097397A and 2108116A which also describe novel classes of aminocyclopentane derivatives. These compounds also inhibit blood platelet aggregation and bronchoconstriction, but this activity is only associated with compounds which have a cyclopentane ring structure which has oxa functions at both the 3- and 5-positions.

We have now found a new group of aminocyclopentane derivatives which do not have an oxa function at the 3-position, but which surprisingly still have very good endoperoxide and thromboxane antagonist activity. The new compounds have a particularly advantageous profile of action, and are of special interest in the treatment of cardiovascular diseases, asthma and adult respiratory distress syndrome and for use in renal transplant and dialysis and in the prevention of relapse of healed peptic ulcers. The synthesis of the new compounds is generally also simpler and less expensive than the syntheses of many 3-oxa substituted aminocyclopentane derivatives previously proposed.

The invention thus provides compounds of the general formulae (1a) and (1b)

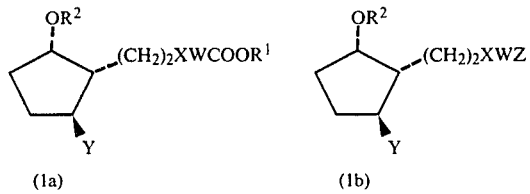

wherein
$R^1$ is a hydrogen atom, or a $C_{1-6}$ alkyl or $C_{7-10}$ aralkyl (e.g. phenalkyl) group;
W is straight or branched $C_{1-7}$ alkylene;
X is cis or trans —CH=CH—;
Y is a saturated heterocyclic amino group (attached to the cyclopentane ring via the nitrogen atom) which has 5–8 ring members and (a) optionally contains in the ring —O—, —S—, —$SO_2$—, or —$NR^3$ (where $R^3$ is a hydrogen atom, $C_{1-7}$ alkyl or aralkyl having a $C_{1-4}$ alkyl portion); and/or (b) is optionally substituted by one or more $C_{1-4}$ alkyl groups;
$R^2$ is (i) straight or branched $C_{1-5}$ alkyl substituted by (a) phenyl [optionally substituted by $C_{1-6}$ alkyl, $C_{5-7}$ cycloalkyl, phenylaklyl having a $C_{1-3}$ alkyl portion, thienyl, phenyl (optionally substituted by $C_{1-4}$ alkyl, $C_{1-4}$ alkoxy, or phenyl)], (b) thienyl [optionally substituted by $C_{5-7}$ cycloalkyl or phenyl (optionally substituted by $C_{1-3}$ alkyl, $C_{1-3}$ alkoxy or halogen)], or (c) naphthyl (optionally substituted by $C_{1-4}$ alkyl or $C_{1-4}$ alkoxy) or (ii) cinnamyl; and Z is —$CH_2OH$, —CHO or —$CONHR^4$ where $R^4$ is a hydrogen atom or a methyl group; and the physiologically acceptable salts and solvates thereof.

In addition to having a desirable selectivity of action, compounds according to the invention also have the advantage of offering an attractive combination of high potency and good chemical stability. Additionally, compounds according to the invention have a solubility in water which is especially convenient for their formulation for parenteral administration.

The structural formulae herein are to be understood to include the enantiomers of each of the compounds concerned as well as mixtures of the enantiomers including racemates, even though the precise structure as set out only relates to one enantiomer.

The compounds of formula (1a) are generally preferred.

Suitable physiologically acceptable salts of the compounds of general formula (1) include acid addition salts derived from inorganic and organic acids, such as hydrochlorides, hydrobromides, sulphates, phosphates, maleates, tartrates, citrates, 2-chlorobenzoates, p-toluenesulphonates, methanesulphonates, salicylates, fumarates, lactates, hydroxy-naphthalenecarboxylates (e.g. 1-hydroxy- or 3-hydroxy-2-naphthalenecarboxylates)or furoates. The compounds may also form salts with suitable bases. Examples of such salts are alkali metal (e.g. sodium and potassium), alkaline earth metal (e.g. calcium or magnesium), ammonium and substituted ammonium (e.g. dimethylammonium, triethylammonium, 2-hydroxyethyl dimethylammonium, piperazine, N,N-dimethylpiperazine, piperidine, ethylenediamine and choline).

The heterocyclic amino group Y may for example have a 5, 6 or 7-membered ring, e.g. pyrrolidino, piperidino, morpholino, piperazino, thiomorpholino, 1,1-dioxothiomorpholino, homomorpholino and hexamethyleneimino. Examples of the optional substituents ($R^3$) which may be present on a second nitrogen atom in the ring are methyl, ethyl, butyl, hexyl, benzyl, and phenethyl. The carbon atoms of the heterocyclic rings may for example be substituted by methyl, ethyl or butyl.

In general Y is preferably pyrrolidino, piperidino or hexamethyleneimino, optionally substituted by one or two $C_{1-4}$ alkyl (particularly methyl) groups, e.g. 4-methylpiperidino. Compounds of formula (1a) in which Y is piperidino are particularly preferred on account of their potency, stability and solubility characteristics, particularly their potency.

Examples of the group $R^1$ are benzyl and $C_{1-3}$ alkyl groups, e.g. methyl or ethyl. In general, $R^1$ is preferably a hydrogen atom or a methyl group, particularly a hydrogen atom.

Where $R^2$ is a substituted alkyl group, the alkylene portion is preferably a methylene, ethylene or propylene group and in particular is a methylene group.

In $R^2$ groups of the type (i) (a), the phenyl group may be substituted by, for example, methyl, ethyl, t-butyl, cyclohexyl, thienyl, benzyl, phenethyl, or phenyl (optionally substituted by methyl, ethyl, methoxy or butoxy) groups.

In $R^2$ groups of the type (i) (b), the thienyl group may be substituted by, for example, cyclohexyl or phenyl (optionally substituted by methyl, ethyl, methoxy, ethoxy, chloro or bromo) groups.

In general $R^2$ is preferably (i) $C_{1-5}$ alkyl (particularly methyl, ethyl or propyl) substituted by (a) phenyl or phenyl substituted by phenyl ($C_{1-3}$) alkyl, thienyl, phenyl, $C_{1-4}$ alkylphenyl or $C_{1-4}$ alkoxyphenyl, (b) thienyl or phenylthienyl or (c) naphthyl, or (ii) cinnamyl.

Particularly preferred $R^2$ groups are (i) methyl, ethyl or propyl (particularly methyl) substituted by naphthyl, thienyl substituted by phenyl and phenyl substituted (preferably in the para-position) by thienyl, benzyl, phenyl, or phenyl substituted (preferably in the para-position) by methyl or methoxy, or (ii) cinnamyl. Especially preferred $R^2$ groups are benzyl substituted by phenyl, methylphenyl or methoxyphenyl, for example [(1,1'-biphenyl)-4-yl]methyl, [4'-methoxy(1,1'-biphenyl)-4-yl]methyl or [4'-methyl(1,1'-biphenyl)-4-yl]methyl, particularly [(1,1'-biphenyl)-4-yl]methyl.

X is preferably cis —CH=CH—.

W may contain for example 1-5 carbon atoms in a straight or branched chain, and may be for example —(CH$_2$)$_2$— or —(CH$_2$)$_4$—, particularly the former.

In general, the compounds of formula (1) in which the carbon atom carrying the —(CH$_2$)$_2$XWCOOR$^1$-group is in the R configuration (and mixtures containing this isomer) are preferred.

The preferences indicated above apply both separately and in combination with one or more of the other stated preferences. Thus a preferred group of compounds of the invention has the formula (1a) in which:

$R^1$ is a hydrogen atom or a methyl group,
W is —(CH$_2$)$_2$—,
X is cis —CH=CH—, $R^2$ is as defined above with reference to the general definition of the compounds of the invention or is a preferred $R^2$ group as described above, and Y is piperidino, including their physiologically acceptable salts and solvates.

The 1R-isomers of this latter group of compounds are generally preferred, as are compounds in which $R^1$ is a hydrogen atom or methyl (particularly a hydrogen atom) and $R^2$ is $C_{1-3}$ alkyl substituted by phenyl or phenyl substituted by phenyl, $C_{1-4}$ alkylphenyl (e.g. methylphenyl), $C_{1-4}$ alkoxyphenyl (e.g. methoxyphenyl), thienyl or phenyl ($C_{1-3}$) alkyl (e.g. benzyl); naphthalenylmethyl; thienylmethyl; or cinnamyl. Compounds of this group in which $R^2$ is benzyl substituted by phenyl, methylphenyl or methoxyphenyl are particularly preferred. Especially important compounds in this group are those in which $R^2$ is [(1,1'-biphenyl)-4-yl]methyl, [4'-methyl(1,1'-biphenyl)-4-yl]methyl or [4'-methoxy(1,1'-biphenyl)-4-yl]methyl, particularly [(1,1'-biphenyl)-4-yl]methyl.

Particularly important compounds of the invention are:

[1α(Z),2α,5β]-(±)-7-[2-[[(1,1'-biphenyl)-4-yl]methoxy]-5-(1-piperidinyl)cyclopentyl]-4-heptenoic acid;

[1R-[1α(Z),2α,5β]]-(+)-7-[2-[[(1,1'-biphenyl)-4-yl]methoxy]-5-(1-piperidinyl)cyclopentyl]-4-heptenoic acid;

[1α(Z),2α,5β]-(±)-7-[2-[[4'-methoxy(1,1'-biphenyl)-4-yl]methoxy]-5-(1-piperidinyl)cyclopentyl]-4-heptenoic acid, and its 1R isomer;

[1α(Z),2α,5β]-(±)-7-[2-[4-(phenylmethyl)phenylmethoxy]-5-(1-piperidinyl)cyclopentyl]-4-heptenoic acid, and its 1R isomer;

[1α(Z),2α,5β]-(±)-7-[2-([4'-methyl(1,1'-biphenyl)-4-yl]methoxy]-5-(1-piperidinyl)cyclopentyl]-4-heptenoic acid, and its 1R isomer;

[1α(Z),2β,5α]-(±)-7-[2-(1-piperidinyl)-5-[4-(2-thienyl)-phenylmethoxy]cyclopentyl]-4-heptenoic acid, and its 1R isomer;

[1α(Z)2α,5β]-(±)-7-[2-3-[(1,1'-biphenyl)-4-yl]propoxy]-5-(1-piperidinyl)cyclopentyl]-4-heptenoic acid, and its 1R isomer;

and their physiologically acceptable salts (particularly hydrochlorides) and solvates.

Compounds of formulae (1a) and (1b) inhibit blood platelet aggregation, bronchoconstriction and vasoconstriction. A test to determine inhibition of blood platelet aggregation is as described by G. V. Born (Nature 194, 927–929, (1962)) except in that collagen is used instead of ADP as the pro-aggregatory agent. Alternatively, starved guinea pigs are dosed orally with the compound to be tested in a suitable vehicle. Platelet rich plasma is prepared from each animal and aggregation to a range of collagen concentrations is measured after the method of Born. Collagen concentration effect curves for each sample of plasma are calculated and results are expressed as the shift of the curves following treatment with the compound.

The ability of the compounds of the invention to inhibit vasoconstriction or bronchoconstriction is determined using the relevant isolated tissue (e.g. spirally cut rat aortic strip or guineapig lung parenchymal strip) by measuring the effect of the compound to be tested on the contraction of the tissue to [1R-[1α,4α,5β(Z),6α(-1E,3S*)]]-7-[6-(3-hydroxy-1-octenyl)-2-oxabicyclo[2,2,1]hept-5-yl]-5-heptenoic acid (U-46619).

The compounds are thus of interest in the treatment of asthma, and as inhibitors of platelet aggregation and thrombosis for use in renal transplant and dialysis and the treatment or prevention of occlusive vascular diseases such as atherosclerosis, peripheral vascular disease, cerebral vascular disease including transient ischaemic attacks, stroke, pulmonary embolism, diabetic retinopathy, post operative thrombosis, angina and myocardial infarction.

The compounds are also of potential use in the treatment of adult respiratory distress syndrome and the prevention of relapse of healed peptic ulcers.

The compounds may be formulated in a conventional manner for use with one or more pharmaceutical carriers.

For oral administration, the pharmaceutical composition may take the form of, for example, tablets, capsules, powders, solutions, syrups, or suspensions prepared by conventional means with acceptable excipients.

The compounds may be formulated for parenteral administration by continuous infusion. Formulations for injections may be presented in unit dosage form in ampoules, or in multi-dose containers, with an added preservative. The compositions may take such forms as suspensions, solutions or emulsions in oil or aqueous vehicles, and may contain formulatory agents such as suspending, stabilising and/or dispersing agents. Alternatively, the active ingredient may be in powder form for reconstitution before use with a suitable vehicle, e.g. sterile pyrogen-free water.

For administration by inhalation the compounds are conveniently delivered in the form of an aerosol spray presentation from pressurised packs or a nebuliser, or as a cartridge from which the powdered composition may be inhaled with the aid of a suitable device. In the case of a pressurised aerosol the dosage unit may be determined by providing a valve to deliver a metered amount.

For use as antithrombotic agents, the compounds are preferably administered orally, for example in amounts of 0.05 to 10 mg/kg body weight, 1 to 4 times daily, or intravenously, for example in amounts of 0.01 to 25 mg/kg body weight, 1 to 4 times daily.

For use in the treatment of asthma, the compounds may also be administered orally in amounts of 0.05 to 10 mg/kg body weight, 1 to 4 times daily; preferably however they are administered by inhalation at doses varying from 0.02 to 30 mg, preferably 0.02 to 3 mg, 1 to 4 times daily. The compounds may be used in combination with other antiasthmatic agents.

The precise dose administered will of course depend on the age and condition of the patient.

Suitable methods for preparing compounds of formula (1) are described below, the groups $R^1$-$R^4$, W, X and Y being as defined above except where otherwise indicated.

(a) Compounds of formula (1a) may be prepared by reacting a compound of formula (2)

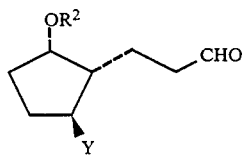

with an appropriate Wittig reagent, e.g. a phosphorane of formula $R_3^5P=CHWCO_2R^1$ (where $R^5$ is $C_{1-6}$ alkyl or aryl, e.g. monocyclic aryl such as phenyl) or a salt thereof, e.g. the potassium salt. Suitable reaction solvents include hydrocarbons (e.g. benzene and toluene), ethers (e.g. tetrahydrofuran) and dialkylsulphoxides (e.g. dimethylsulphoxide). The reaction may be carried out at any suitable temperature from −70° to 50° C., preferably at room temperature.

The reaction is particularly suitable for the preparation of compounds in which $R^1$ is a hydrogen atom.

The intermediate aldehydes of formula (2) may be prepared by the following sequence:

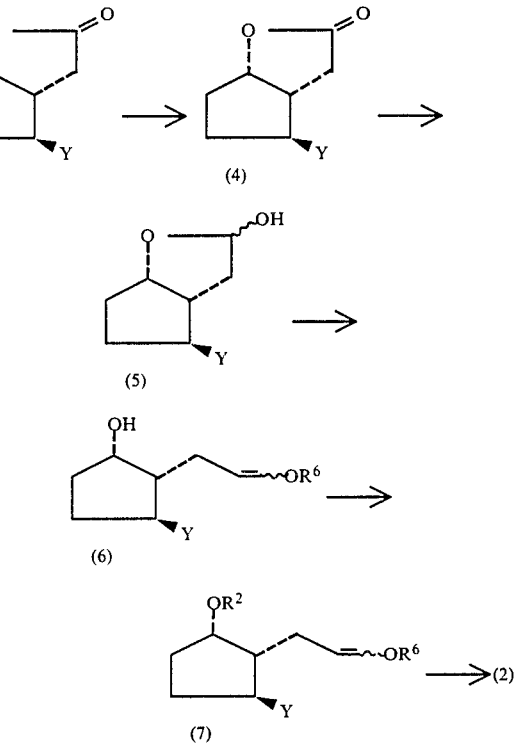

A lactone of formula (4) is prepared from the corresponding lactone (3) by catalytic hydrogenation, using for example a catalyst such as rhodium on charcoal in a solvent such as ethyl acetate. The lactone (4) is the reduced to the corresponding lactols (5), for example with diisobutylaluminium hydride in a solvent such as dichloromethane at a low temperature, e.g. −78° C. These are then treated with an appropriate Wittig reagent (e.g. $R_3^5P=CHOR^6$, where $R^5$ is as defined above and $R^6$ is $C_{1-4}$ alkyl), as described for process (a) above, to give the hydroxy compound (6). The group $R^2$ is then introduced by etherification of the hydroxy compound (6) with an appropriate reagent $R^2L$ (where L is a leaving group, e.g. halogen or tosylate), for example by reaction at room temperature in the presence of a suitable base (e.g. sodium hydride) in a suitable solvent (e.g. dimethylformamide). The resulting vinyl ether (7) is then hydrolysed to give the desired aldehyde (2), for example using a dilute acid such as hydrochloric acid in a suitable solvent (e.g. acetone).

Lactones of formula (3) may be prepared by the method described in UK Patent Specification No. 2028805A using the appropriate amine YH.

In another process, the vinyl ethers of formula (7) may be prepared by a sequence of reactions involving dehydroxylation and subsequent modification of an intermediate cyclopentanol as described in the experimental section at the end of this specification.

(b) Compounds of formula (1a) in which $R^1$ is a hydrogen atom may be prepared by hydrolysing a corresponding ester, amide or nitrile.

The hydrolysis of the above starting materials can in general be effected by conventional methods under acidic or basic conditions, for example in an organic or aqueous organic solvent at any suitable temperature up to and including reflux. Suitable bases include inorganic bases such as alkali metal hydroxides (e.g. NaOH), alkali metal carbonates (e.g. $K_2CO_3$) and alkaline earth metal hydroxides (e.g. $Ba(OH)_2$). Suitable organic bases include tetra alkylammonium hydroxides [e.g. $(^nBu)_4N^+OH^-$]. Suitable acids include inorganic acids such as hydrochloric acid and organic acids such as trifluoroacetic acid and acetic acid. Suitable solvents include ethers (e.g. diethyl ether, dioxan and tetrahydrofuran), halogenated hydrocarbons (e.g. $CH_2Cl_2$), hydrocarbons (e.g. toluene), dipolar aprotic solvents (e.g. acetone, acetonitrile, dimethylsulphoxide and dimethylformamide) and alcohols (e.g. methanol, ethanol and ethylene glycol). Where desired the solvents may be used in combination with water.

The specific hydrolysis method will of course depend on the particular nature of the starting material.

The acid of formula (1a) produced may be isolated in the form of a salt, for example a salt with an inorganic acid, such as hydrochloric acid. This is particularly convenient and advantageous when the hydrolysis is effected with the same acid; salt formation and hydrolysis then take place in the same reaction step.

The starting materials for this process may for example be corresponding compounds of formula (8)

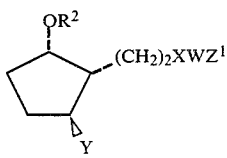

(8)

where $Z^1$ is (a) $-COOR^{1a}$ where $R^{1a}$ is di- or tri-arylmethyl (e.g. di- or triphenylmethyl), trihydrocarbylsilyl (e.g. diphenyl-t-butylsilyl), $-CH_2CCl_3$, $-CH_2CH=CH_2$, $C_{1-6}$ alkyl (optionally substituted at the α-position by $C_{1-6}$ alkoxy or $C_{1-6}$ alkylthio) or a 5- or 6-membered cycloalkyl group containing —O— in the ring (e.g. tetrahydrofuran-2-yl or tetrahydropyran-2-yl (b) $-CONR_2^7$ where $R^7$ is —H or $C_{1-4}$ alkyl, or (c) —CN.

Suitable examples of $R^{1a}$ groups are:

(1) $-CR^8R^9R^{10}$ in which $R^8$ and $R^9$ are each phenyl (optionally substituted by $C_{1-4}$ alkyl, $C_{1-4}$ alkoxy, di-($C_{1-4}$)alkylamino, nitro or halogen) and $R^{10}$ is a hydrogen atom or a substituted or unsubstituted phenyl group as defined for $R^8$ and $R^9$;

(2) $-SiR^{11}R^{12}R^{13}$ where $R^{11}$, $R^{12}$ and $R^{13}$ are aryl (e.g. phenyl) or $C_{1-6}$ alkyl;

(3) $-CH_2CCl_3$;

(4) $-CH_2CH=CH_2$;

(5) $-CH(R^{14})BCH_2R^{15}$ where B is —O— or —S—, and where $R^{14}$ and $R^{15}$ are —H or $C_{1-4}$ alkyl (e.g. $-CH_2OCH_3$, $-CH(CH_3)OCH_2CH_3$ or $-CH_2SCH_3$) or where $R^{14}$ and $R^{15}$ together represent $-(CH_2)_2-$ or $-(CH_2)_3-$ and B is —O—; and (6) $C_{1-6}$ alkyl.

Specific examples of the groups of the type (1), include triphenylmethyl (in which the phenyl groups are optionally substituted by methyl, methoxy or nitro) or diphenylmethyl (in which the phenyl groups are optionally substituted by halogen, methyl, methoxy or dimethylamino).

The latter group of esters (and other esters in which $Z^1$ is a group of the type (a)) may be hydrolysed by the methods described above. The process is particularly useful in preparing a salt of a compound of formula (1a) by treating a compound of formula (8) (e.g. a compound in which $Z^1$ is a group (a), particularly where $R^{1a}$ is a group (1), e.g. triphenylmethyl) with an acid or a base. Thus for example a hydrochloride of a compound of formula (1a) may be prepared by treating a solution of the compound of formula (8) as just mentioned with hydrogen chloride or hydrochloric acid. This method is particularly suitable in the preparation of the preferred compounds of formula (1a) described above. Esters in which $R^{1a}$ is a group (2) may also be removed using a fluoride (e.g. tetra-n-butylammonium fluoride, KF or HF), for example using tetrahydrofuran or aqueous $CH_3CN$ as the reaction solvent.

Esters in which $R^{1a}$ is $-CH_2CCl_3$ may also be removed by reduction e.g. with a metal such as zinc under mildly acidic conditions for example using an aqueous phosphate buffer. Tetrahydrofuran, dioxan and dimethoxyethane are suitable solvents.

When $R^{1a}$ is a group of type (5) and B is S, hydrolysis may also be effected in the presence of $Hg^{II}$ salts e.g. mercuric trifluoroacetate for example using aqueous $CH_3CN$ as solvent. These esters may also be hydrolysed in the presence of $Ag^{II}$ salts (e.g. $AgNO_3$), for example using aqueous tetrahydrofuran, dioxan, dimethoxyethane or $CH_3CN$ as solvent.

The hydrolysis of the derivatives of formula (8) in which $Z^1$ is a group of the type (b) or (c) can in general be effected using an inorganic base (e.g. KOH) in a suitable solvent such as aqueous ethanol or ethylene glycol at a temperature up to and including reflux.

The starting materials for process (b) may be prepared from the corresponding carboxylic acid (i.e. the compound of formula (1a) in which $R^1$ is —H) by conventional methods, for example as described in UK Patent Specification 2129796A. Alternatively, the $Z^1$ group may be introduced by use of a Wittig reagent of the formula $R_3^5P=CHWZ^1$ in process (a) above.

(c) Compounds of formula (1a) in which $R^1$ is $C_{1-6}$ alkyl or $C_{7-10}$ aralkyl may be prepared by esterification of the corresponding carboxylic acid. Conventional esterification techniques may be used, for example by reaction with an appropriate alcohol in the presence of a mineral acid such as hydrochloric acid or sulphuric acid.

Alternatively the acid may be converted into an activated derivative (e.g. a corresponding mixed anhydride) e.g. by reaction with an alkyl chloroformate (e.g. isobutyl chloroformate) in the presence of a suitable base, e.g. triethylamine or pyridine. The activated derivative can then be reacted with an appropriate alcohol, for example using a solvent such as acetone and a temperature of $-10°$ C. to room temperature.

(d) Compounds of formula (1a) may be prepared by dehydroxylation (homolytic cleavage of the carbonoxygen bond) of a corresponding alcohol of formula (9)

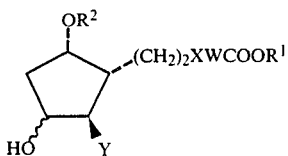

(9)

for example via tri-n-butyltin hydride reduction of a thioester derivative such as the thiocarbonyl imidazolide. The reaction is particularly suitable for the preparation of compounds in which $R^1$ is alkyl or aralkyl.

The reduction is preferably carried out in a hydrocarbon solvent (e.g. toluene) at a temperature up to and including reflux in the presence of a radical initiator e.g. azobisisobutyronitrile.

The thioester derivative may be conventionally prepared from the alcohol (9) using a suitable reagent (e.g. 1,1'-thiocarbonyldiimidazole) in a suitable solvent (e.g. tetrahydrofuran) at room temperature.

Alcohols of formula (9) may be prepared by the methods generally described in UK Patent Specifications 2075503A and 2097397A.

(e) Compounds of formula (1a) may also be prepared by reduction of a corresponding compound of formula (1a) in which X is an acetylene group. Suitable methods of reduction include using hydrogen in the presence of a catalyst e.g. palladium on a support (e.g. $CaCO_3$ or $BaSO_4$) and poisoned for example by lead or quinoline. Suitable solvents include ethyl acetate and methanol. This reaction is particularly suitable for preparing compounds in which X is cis—CH=CH—.

Compounds of formula (1a) in which X is an acetylene group may be prepared from compounds of formula (9) in which X is an acetylene group using the method described in (d) above.

Compounds of formula (9) in which X is an acetylene group may be prepared by the methods generally described in UK Patent Specifications 2075503A and 2097397A.

(f) Compounds of formula (1a) in which X is trans —CH=CH— may be prepared by isomerising the corresponding cis compound. The isomerisation may for example be effected by treatment with p-toluene sulphinic acid in dioxan (e.g. at reflux) or azobisisobutyronitrile and thiophenol, using for example a hydrocarbon solvent (e.g. benzene) and any suitable temperature up to reflux.

(g) Compounds of formula (1a) in which $R^1$ is a hydrogen atom may also be prepared by oxidising the corresponding aldehyde or primary alcohol (i.e. a compound of formula (1b) in which Z is —CHO or $CH_2OH$.

Suitable methods of oxidation include using a $Cr^{VI}$ oxidising agent in a suitable solvent, e.g. chromic acid in acetone (e.g. Jones reagent, preferably used in the presence of a diatomaceous silica such as Celite) or $CrO_3$ in pyridine. These reagents are for example used at temperatures of −20° C. to room temperature.

The oxidation may also be effected with oxygen in the presence of a catalyst such as platinum dioxide in a suitable solvent (e.g. acetone) at an elevated temperature (e.g. 50° C.).

(h) Compounds of formula (1b) in which Z is —CH$_2$OH may be prepared by reducing a corresponding compound of formula (1a) in which $R^1$ is a methyl group, for example with $LiAlH_4$.

(i) Compounds of formula (1b) in which Z is —CHO may be prepared by oxidising the corresponding compound of formula (1b) in which Z is —CH$_2$OH, using for example an activated sulphur reagent, e.g. (i) N-chlorosuccinimide-dimethylsulphide complex in a suitable solvent (e.g. toluene or dichloromethane) at temperatures of for example −25° to 25° C., preferably at 0°–5° C., or (ii) pyridine —SO$_3$ complex in dimethylsulphoxide, preferably at 0° C. to room temperature.

(j) Compounds of formula (1b) in which Z is —CONHR$^4$ may be prepared by amidation of the parent carboxylic acid i.e. the corresponding compound of formula (1a) in which $R^1$ is a hydrogen atom.

Conventional methods for converting acids into amides may be used, for example by treating the acid with isobutylchloroformate in the presence of triethylamine and reacting the resulting reactive derivative of the carboxylic acid with ammonia or an amine $R^4NH_2$.

(k) Where salts of compounds of the invention are desired such salts may be formed by conventional methods, for example by treatment with an acid or with a base.

Treatment may for example be effected in a suitable solvent such as an ether (e.g. diethylether), acetonitrile, acetone, chloroform, dichloromethane, ethyl acetate, iso-propyl acetate or an alcohol, e.g. methanol, ethanol or iso-propanol.

Salts may also be formed by conversion of one salt of a compound of the invention into another, e.g. by ion exchange using conventional methods.

When a specific enantiomer of formula (1) is required, starting materials having the desired stereochemical configuration should be used in the above processes. Such starting materials may be prepared for example from an enantiomeric bicycloheptenone as described in European Patent Specification 74856 using the methods generally described in UK Patent Specifications 2028805A, 2075503A and 2097397A.

The following examples illustrate the invention.

Temperatures are in °C. 'Dried' refers to drying with MgSO$_4$. 'Hyflo' is a filtration aid. Chromatography and thin layer chromatography (t.l.c.) are using silica gel unless stated otherwise. The following abbreviations are used:

THF—tetrahydrofuran
DMF—dimethylformamide
Dibal—diisobutylaluminium hydride (1M in hexane)
DMSO—dimethylsulphoxide
EA—ethyl acetate
ER—diethyl ether
PE—petroleum ether (b.p. 40°–60°)
IPA—isopropyl acetate
AIBN—azobisisobutyronitrile The preparations of the following intermediates are described in British Patent Specification 2097397A.

Intermediate 1

[1R-(endo,anti)]-(−)-6-[[(1,1'-Biphenyl)-4-yl]methoxy]-8-(1-piperidinyl)-2-oxabicyclo[3.2.1]octan-3-one.

Intermediate 2

[1R-[1α(Z),2β,3β,5α]]-(+)-Methyl 7-[5-[[(1,1'-Biphenyl)-4-yl]methoxy]3-hydroxy-2-(1-piperidinyl)-cyclopentyl]-4-heptenoate.

Intermediate 3

[1R-[1α-(Z),2β,3β,5α]]-(+)-7-[5-[[(1,1'-Biphenyl)-4-yl]methoxy]-3-hydroxy-2-(4-morpholinyl)cyclopentyl]-4-heptenoic acid.

Intermediate 4

[1R-[1α(Z),2β,3β,5α]]-(+)-7-[5-[[(1,1'-Biphenyl)-4-yl]methoxy]-3-hydroxy-2-(1-piperidinyl)cyclopentyl]-4-heptenoic acid.

The preparation of the following intermediate is described in British Patent Specification No. 2129796A.

Intermediate 5

[1R-[1α(Z),2β,3α,5α]]-(+)-Methyl 7-[3-Hydroxy-5-[[4'-methoxy(1,1'-biphenyl)-4-yl]methoxy]-2-(1-piperidinyl)cyclopentyl]-4-heptenoate, hydrochloride.

Intermediate 6

[1R-[1α(Z),2β,3β,5α]]-(+)-Methyl 7-[5-[[(1,1'-Biphenyl)-4-yl]methoxy]-3-hydroxy-2-(4-morpholinyl)cyclopentyl]-4-heptenoate A solution of Intermediate 3, hydrochloride (1.35 g) in 19:1 methanol conc. $H_2SO_4$ (10 ml) was kept at ambient temperature for 18 h, then diluted with 8% $NaHCO_3$ solution (100 ml) and extracted with $CH_2Cl_2$ (3×25 ml). The combined extracts were dried and evaporated and the residue was purified by chromatography using ER then 19:1 ER-methanol as eluant to give the title compound as an oil (0.96 g).

I.r. ($CHBr_3$) 3550, 3460–3200, 1728 cm$^{-1}$.

$[\alpha]_D^{21.4} = +78.2°$ ($CHCl_3$).

Intermediate 7

[1R-[1α(Z),2β,5α]]-(−)-Methyl 7-[5-[[4'-Methoxy(1,1'-biphenyl)-4-yl]methoxy]-3-oxo-2-(1-piperidinyl)cyclopentyl]-4-heptenoate A solution of pyridine-sulphur trioxide complex (10.33 g) in dry DMSO (17 ml) was added to a cold (0°) solution of Intermediate 5, base (8.47 g) in $Et_3N$ (13.5 ml), $CH_2Cl_2$ (30 ml) and DMSO (20 ml). After 1 h at 0° the mixture was diluted with pH 6.5 phosphate buffer (140 ml) and extracted with EA (3×50 ml). The combined extracts were dried and evaporated and the residue was purified by chromatography using 1:3 EA-PE as eluant to give the title compound as a solid (5.69 g). A portion was recrystallized from ER-PE m.p. 61.5°–62.5°.

$[\alpha]_D^{22.2} = -19.8°$ ($CHCl_3$).

Intermediate 8

[1R-[1α(Z),2β,3β,5α]]-(+)-Methyl 7-[3-Hydroxy-5-[[4'-methoxy(1,1'-biphenyl)-4-yl]methoxy]-2-(1-piperidinyl)cyclopentyl]-4-heptenoate Dibal (93 ml) was added dropwise to a cold (−5°) stirred solution of 2,6-di-tert-butyl-4-methylphenol (30.75 g) in dry toluene (350 ml). After 1 h at −5° the mixture was cooled to −70° and a solution of Intermediate 7 (9.67 g) in toluene (50 ml) was added dropwise. After 1 h at −70° and 1 h at −10° the mixture was washed with 2N HCl (7×60 ml) and the toluene was discarded. The acidic extracts were neutralised with 5N NaOH solution (200 ml) and extracted with $CH_2Cl_2$ (4×80 ml). The combined extracts were dried and evaporated and the residue was purified by chromatography using 17:3 ER-methanol as eluant to give the title compound (7.02 g) as an oil.

Analysis Found: C, 73.5; H, 8.5; N, 2.7. $C_{32}H_{43}NO_5$ requires C, 73.7; H, 8.3; N, 2.7%.

$[\alpha]_D^{21} = +63.2°$ ($CHCl_3$).

Intermediate 9

[1R-(1α,2β,3α,5α)]-(+)-Methyl 5-[[(1,1'-Biphenyl)-4-yl]methoxy]-3-hydroxy-2-(1-piperidinyl)cyclopentaneacetate A solution of Intermediate 1 (3.5 g) in methanol (50 ml) and ethereal HCl (50 ml) was kept at ambient temperature for 20 h. The solvents were removed in vacuo and the residue in 8% $NaHCO_3$ solution (100 ml) was extracted with $CH_2Cl_2$ (4×75 ml). The combined extracts were dried and evaporated to give a solid (3.78 g).

A portion was crystallised from EA-PE to give the title compound m.p. 105°–107°.

$[\alpha]_D = +66°$ ($CHCl_3$).

Intermediate 10

(a) [1R-[1α(Z),2β,3β,5α]]-(+)-Methyl 7-5-[[(1,1'-Biphenyl)-4-yl]methoxy]-3-[(1H-imidazol-1-yl)thioxomethoxy]-2-(1-piperidinyl)cyclopentyl]-4-heptenoate A solution of Intermediate 2 (3.1 g) and 1,1'-thiocarbonyldiimidazole (1.35 g) in dry THF (12 ml) was kept at ambient temperature for 2 h then the solvent was removed in vacuo. The residue in EA (100 ml) was washed with pH 6 phosphate buffer, dried and the solvent evaporated to give the title compound as an oil (3.7 g). T.l.c. ER Rf 0.37.

The following compounds were prepared in a similar manner:

(b) [1R-(1α,2β,3α,5α)]-(+)-Methyl [5-[[(1,1'-Biphenyl)-4-yl]methoxy]-3-[(1H-imidazol-1-yl)thioxomethoxy]-2-(1-piperidinyl)]cyclopentaneacetate, m.p. 94°–98° from Intermediate 9.

(c) [1R-[1α(Z),2β,3β,5α]]-(+)-Methyl 7-[5-[[(1,1'-Biphenyl)-4-yl]methoxy]-3-[(1H-imidazol-1-yl)thioxomethoxy]-2-(4-morpholinyl)cyclopentyl]-4-heptenoate, from Intermediate 6. T.l.c. EA Rf 0.47.

(d) [1R-[1α(Z),2β,3β,5α]]-(+)-Methyl 7-[3-[(1H-Imidazol-1-yl)thioxomethoxy]-5-[[4'-methoxy(1,1'-biphenyl)-4-yl]methoxy]-2-(1-piperidinyl)cyclopentyl]-4-heptenoate from Intermediate 8. T.l.c. ER Rf 0.36.

Intermediate 11

[1R-(1α,2α,5β)]-(+)-Methyl 2-[[(1,1'-Biphenyl)-4-yl]methoxy]-5-(1-piperidinyl)cyclopentaneacetate A solution of AIBN (0.91 g) and tri-n-butyltin hydride (22.72 g) in toluene (80 ml) was added over 10 min to a stirred suspension of Intermediate 10b (25.5 g) in toluene (250 ml) at 95°–100° under nitrogen. After a further 15 min at 100° the mixture was concentrated in vacuo and the mixture was purified by chromatography eluting initially with 19:1 PE-ER to remove impurities then with 25:25:1 PE-ER-$Et_3N$ to give the title compound as a solid (9.12 g). A portion was crystallised from ethanol-PE m.p. 113°–116°.

$[\alpha]_D^{23} = +74.4°$ ($CHCl_3$).

Intermediate 12

[1R-(1α,2α,5β)]-(+)-2-[[(1,1'-Biphenyl)-4-yl]methoxy]-5-(1-piperidinyl)cyclopentaneethanol, hydrochloride Dibal (75 ml) was added over 0.5 h to a cooled (−65°), stirred solution of Intermediate 11 (8.27 g) in $CH_2Cl_2$ (200 ml) under nitrogen. The solution was allowed to warm to 0° over 2 h then methanol (200 ml)

was added. After a further 1 h, the mixture was filtered and the filtrate was evaporated in vacuo. The residue was dissolved in ER (300 ml), filtered and evaporated to give the title compound, base (7.06 g). A portion in ER was treated with an excess of ethereal HCl and the resulting solid was crystallised from $CH_2Cl_2$-IPA to to give the title compound m.p. 165°–168°.

$[\alpha]_D^{22} = +56°$ (CHCl$_3$).

Intermediate 13

[1R-(1α,2α,5β)]-(+)-2-[[(1,1'-Biphenyl)-4-yl]methoxy]-5-(1-piperidinyl)cyclopentaneacetaldehyde A solution of pyridine-sulphur trioxide complex (0.5 g) in DMSO (3 ml) was added to a cooled (5°), stirred solution of Intermediate 12 (0.397 g) and Et$_3$N (0.72 ml) in $CH_2Cl_2$ (5 ml). After 1 h the mixture was diluted with 30% NH$_4$Cl solution (10 ml) and the layers separated. The aqueous layer was extracted with $CH_2Cl_2$ (2×7 ml) and the combined extracts were dried and evaporated. The residue was purified by chromatography to give the title compound as an oil (0.18 g).

I.r. (CHBr$_3$) 2740, 1710 cm$^{-1}$.

$[\alpha]_D^{25} = +100.7°$ (CHCl$_3$).

Intermediate 14

(a) (3aα,4α,6aα)-(±)-3,3a,4,6a-Tetrahydro-4-(1-piperidinyl)-2H-cyclopenta[b]furan-2-one Piperidine (8.4 g) was added to a cold (0°), stirred solution of (3aα,6α,6aα)-6-bromo-3,3a,6,6a-tetrahydro-2H-cyclopenta[b]furan-2one (5.1 g) in acetone (60 ml) and the mixture was stirred at ambient temperature for 20 h. The mixture was poured into water (200 ml) and saturated NaCl (100 ml) and extracted with EA (3×100 ml). The aqueous layer was adjusted to pH 9 and re-extracted with EA (2×100 ml). The combined extracts were dried and evaporated and the residue was purified by chromatography using 4:1 EA-methanol as eluant to give the tital compound as an oil (3.2 g). I.r. (CHBr$_3$) 1760 cm$^{-1}$.

The following compounds were prepared in a similar manner:

(b) (3aα,4α,6aα)-(±)-3,3a,4,6a-Tetrahydro-4-(4-thiomorpholinyl)-2H-cyclopenta[b]furan-2-one, m.p. 87°–89° using thiomorpholine and diisopropylethylamine. Purification by crystallisation from $CH_2Cl_2$-ER-PE.

(c) (3aα,(4α,6)aα)-(±)-3,3a,4,6a-Tetrahydro-4-(4-methyl-1-piperazinyl)-2H-cyclopenta[b]furan-2-one, m.p. 62°–64° using N-methylpiperazine and diisopropylethylamine. Purification by crystallisation from PE-ER.

(d) (3aα,4α,6aα)-(±)-3,3a,4,6a-Tetrahydro-4-(4-methyl-1piperidinyl)-2H-cyclopenta[b]furan-2-one, using 4-methylpiperidine. Purification by chromatography on Et$_3$N deactivated silica using EA as eluant. I.r. (CHBr$_3$) 1760 cm$^{-1}$.

(e) (3aα,4α,6aα)-(±)-3,3a,4,6a-Tetrahydro-4-(1-pyrrolidinyl)-2H-cyclopenta[b]furan-2-one, using pyrrolidine. Purification by chromatography using 79:20:1 EA-methanol-Et$_3$N as eluant.

I.r. (CHBr$_3$) 1765 cm$^{-1}$.

(f) (3aα,4α,6aα)-(±)-3,3a,4,6a-Tetrahydro-4-(Hexahydro-1H-azepin-1-yl)-2H-cyclopenta[b]furan-2-one, using hexahydro-1H-azepine. Purification by chromatography on Et$_3$N deactivated silica using initially 1:1 $CH_2Cl_2$-ER then ER as eluant. I.r. (CHBr$_3$) 1760 cm$^{-1}$.

Intermediate 15

(3aα,4α,6aα)-(±)-3,3a,4,6a-Tetrahydro-4-(4-thiomorpholinyl)-2H-cyclopenta[b]furan-2-one, S,S-dioxide Peracetic acid (6.14 molar in acetic acid; 5 ml) was added dropwise to a stirred solution of Intermediate 14b (1 g) in $CH_2Cl_2$ (10 ml). After 72 h the mixture was added dropwise to 20% Na$_2$SO$_3$ solution (20 ml) and the mixture was stirred at ambient temperature for 1 h. The layers were separated and the aqueous layer was extracted with $CH_2Cl_2$ (2×20 ml). The combined organic layers were washed with 8% NaHCO$_3$ solution (20 ml) dried and evaporated. A portion of the residual solid (1.02 g) was crystallised from EA-methanol to give the title compound m.p. 147°–150°.

Intermediate 16

(a) (3aα,4α,6aα)-(±)-Hexahydro-4-(1-piperidinyl)-2H-cyclopenta[b]furan-2-one, hydrochloride A solution of Intermediate 14a (7.8 g) in EA (100 ml) was hydrogenated over a pre-reduced suspension of 5% Rhodium on charcoal in EA (100 ml) for 5 h at atmospheric pressure and ambient temperature. The catalyst was removed by filtration (Hyflo) and the filtrate was washed with 8% NaHCO$_3$ solution (50 ml) dried and evaporated to give an oil (2.9 g). A portion in ER was treated with an excess of ethereal HCl and the resulting solid was recrystallised from methanol-EA to give the title compound m.p. 198°–199°.

The following compounds were prepared in a similar manner:

(b) (3aα,4α,6aα)-(±)-Hexahydro-4-(4-methyl-1-piperazinyl)-2H-cyclopenta[b]furan-2-one, m.p. 93°–96° from Intermediate 14c using 5% Rhodium on alumina. Purification by crystallisation from EA-PE.

(c) (3aα,4α,6aα)-(±)-Hexahydro-4-(4-methyl-1-piperidinyl)-2H-cyclopenta[b]furan-2-one, from Intermediate 14d using 5% Rhodium on alumina in ethanol. I.r. (CHBr$_3$) 1760 cm$^{-1}$.

(d) (3aα,4α,6aα)-(±)-Hexahydro-4-(1-pyrrolidinyl)-2H-cyclopenta[b]furan-2-one, m.p. 47°–50° from Intermediate 14e using 5% Rhodium on alumina in ethanol. Purification by chromatography on Et$_3$N deactivated silica using EA as eluant.

(e) (3aα, 4α,6aα)-(±)-Hexahydro-4-(4-thiomorpholinyl)-2H-cyclopenta[b]furan-2-one S,S-dioxide, m.p. 167°–171° from Intermediate 15 using 5% Rhodium on charcoal in methanol-water. Purification by crystallization from EA-methanol.

Intermediate 17

(3aα,4α,6aα)-(±)-Hexahydro-4-(Hexahydro-1H-azepin-1-yl)-2H-cyclopenta[b]furan-2-one A solution of Intermediate 14f (1.1 g) in 5N NaOH (10 ml) and water (60 ml) was hydrogenated over presaturated 5% Rhodium on charcoal (250 mg) in water (30 ml). After uptake of hydrogen had ceased the catalyst was removed by filtration (Hyflo) and conc. HCl (15 ml) was added to the filtrate. After 3 h the solution was basified with 25% K$_2$CO$_3$ solution and extracted with $CH_2Cl_2$ (3×40 ml). The combined extracts were dried and evaporated and the residue in ER was filtered and the solvent removed to give the title compound as an oil (1.04 g).

I.r. (CHBr$_3$) 1760 cm$^{-1}$.

Intermediate 18

(a) (3aα,4α,6aα)-(±)-Hexahydro-4-(1-piperidinyl)-2H-cyclopenta[b]furan-2-ol

A solution of Intermediate 16a (8.3 g of base) in CH$_2$Cl$_2$ (40 ml) was stirred at −78° under nitrogen whilst Dibal (60 ml) was added slowly. After 2 h methanol (40 ml) was added slowly and the mixture was allowed to attain ambient temperature and then was stirred for 18 h. The solids were removed by filtration (Hyflo) and the filtrate was evaporated in vacuo to give the title compound (7.6 g) m.p. 77°–81°.

The following compounds were prepared in a similar manner:
(b) (3aα,4α,6aα)-(±)-Hexahydro-4-(4-methyl-1-piperidinyl)-2H-cyclopenta[b]furan-2-ol, m.p. 80°–85° from Intermediate 16c.
(c) (3aα,4α,6aα)-(±)-Hexahydro-4-(4-methyl-1-piperazinyl)-2H-cyclopenta[b]furan-2-ol, from Intermediate 16b.
I.r. (CHBr$_3$) 3580 cm$^{-1}$.
(d) (3aα,4α,6aα)-(±)-Hexahydro-4-(4-thiomorpholinyl)-2H-cyclopenta[b]furan-2-ol S,S-dioxide, from Intermediate 16e. I.r. (CHBr$_3$) 3580 cm$^{-1}$.
(e) (3aα,4α,6aα)-(±)-Hexahydro-4-(1-pyrrolidinyl)-2H-cyclopenta[b]furan-2-ol, m.p. 79°–82° from Intermediate 16d.
(f) (3aα,4α,6aα)-(±)-Hexahydro-4-(hexahydro-1H-azepin-1-yl)-2H-cyclopenta[b]furan-2-ol, from Intermediate 17. I.r. (CHBr$_3$) 3580 cm$^{-1}$.

Intermediate 19

(a) (1α,2α,3β)-(±)-2-(3-Methoxy-2-propenyl)-3-(1-piperidinyl)cyclopentanol (Methoxymethyl)triphenylphosphonium chloride (16.5 g) was added in portions to a stirred solution of potassium t-butoxide (5.6 g) in dry THF at 0°. After 0.5 h a solution of Intermediate 18a (3.5 g) in dry THF (20 ml) was added dropwise and stirring continued for 2 h. The mixture was poured into 8% NaHCO$_3$ solution (250 ml) and the organic layer separated. The aqueous layer was extracted with CH$_2$Cl$_2$ (3×100 ml) and the combined organic layers were dried and evaporated. The residue was purified by chromatography using initially 9:1 EA-methanol then 85:100:5 EA-methanol-Et$_3$N as eluent to give the title compound as an oil (3.5 g). I.r. (CHBr$_3$) 3600, 3500, 1655 cm$^{-1}$.

The following compounds were prepared in a similar manner:
(b) [2R-(1α,2β,3β)]-(+)-1-[3-[[(1,1′-Biphenyl)-4-yl]methoxy]-2-(3-methoxy-2-propenyl)cyclopentyl]piperidine, m.p. 44°–47° from Intermediate 13. Purification by chromatography using initially 1:1 PE-ER then 25:75:1 PE-ER-Et$_3$N as eluant.
[α]$_D^{25}$ = +74.5° (CHCl$_3$).
(c) (1α,2α,3β)-(±)-2-(3-Methoxy-2-propenyl)-3-(4-methyl-1-piperidinyl)cyclopentanol, from Intermediate 18b. Purification by chromatography using 99:1 EA-Et$_3$N as eluant then rechromatography using 19:1:0.1 CH$_2$Cl$_2$-methanol-Et$_3$N as eluant.
I.r. (Film) 3400, 1652 cm$^{-1}$.
(d) (1α,2α,3β)-(±)-(3-Methoxy-2-propenyl)-3-(4-methyl-1-piperazinyl)cyclopentanol, from Intermediate 18c. Purification by chromatography using initially 49:1 EA-Et$_3$N then 75:25:2 EA-methanol-Et$_3$N as eluant. I.r. (Film) 3400(br), 1660 cm$^{-1}$.
(e) (1α,2α,3β)-(±)-(3-Methoxy-2-propenyl)-3-(4-thiomorpholinyl)cyclopenta S,S-dioxide, from Intermediate 18d. Purification by chromatography using initially 4:1 EA-PE then EA as eluant.
I.r. (Film) 3400 (br), 1655 cm$^{-1}$.
(f) (1α,2α,3β)-(±)-2-(Methoxy-2-propenyl)-3-(1-pyrrolidinyl)cyclopentanol, from Intermediate 18e. Purification by chromatography using 80:20:1 EA-methanol-Et$_3$N as eluant.
I.r. (Film) 3400 (br), 1650 cm$^{-1}$.
(g) (1α,2α,3β)-(±)-3-(Hexahydro-1H-azepin-1-yl)-2-(3-methoxy-2-propenyl)cyclopentanol, from Intermediate 18f. Purification by chromatography on activity 2 alumina using ER as eluant.
I.r. (Film) 3450 (br), 1655 cm$^{-1}$.

Intermediate 20

(1α,2β,3β)-(±)-1-[3-[[(1,1′-Biphenyl)-4-yl]methoxy]-2-(3-methoxy-2-propenyl)cyclopentyl]piperidine 4-Bromomethyl(1,1′-biphenyl) (4.9 g) was added to a cold (0°) stirred mixture of Intermediate 19a (1.7 g) and sodium hydride (0.64 g, 80% dispersion in oil) in dry DMF (3 ml). After 3 h at ambient temperature the mixture was poured carefully into water (30 ml) and extracted with CH$_2$Cl$_2$ (3×30 ml). The combined extracts were dried and evaporated and the residue was purified by chromatography using initially 9:1 EA-methanol then 85:10:5 EA-methanol-Et$_3$N as eluant to give the title compound as an oil (1.45 g).

Analysis Found: C, 79.7; H, 8.6; N, 3.6. C$_{27}$H$_{35}$NO$_2$ requires C, 80.0; H, 8.7; N, 3.45%.

Intermediate 21

(1α,2β,3β)-(±)-1-[3-[4-(1,1-Dimethylethyl)phenylmethoxy]-2-(3-methoxy-2-propenyl)cyclopentyl]piperidine NaOH powder (403 mg) was added under nitrogen to a stirred solution of Intermediate 19a (200 mg) in dry DMSO (2 ml). After 10 min 1-bromomethyl-4-(1,1-dimethylethyl)benzene (210 mg) was added and stirring continued for 4 h. The mixture was diluted with pH 6.5 phosphate buffer (30 ml) and extracted with EA (3×20 ml). The combined extracts were dried and evaporated and the residue was purified by chromatography using 4:1 EA-methanol to give the title compound (200 mg). T.l.c. 4:1 EA-methanol Rf 0.41.

Intermediate 22

(a) (1α,2β,3β)-(±)-1-[2-(3-Methoxy-2-propenyl)-3-[[4-(phenylmethyl)phenyl]methoxy]cyclopentyl]piperidine Sodium Hydride [60% dispersion in oil ) 240 mg] was added to a stirred solution of Intermediate 19a (0.72 g) in dry DMF (10 ml). The mixture was heated to ca. 80° to complete hydrogen evolution and then cooled (0°) whilst 1-(bromomethyl)-4-(phenylmethyl)benzene (0.78 g) was added. After 2 h the mixture was diluted with brine (200 ml) and extracted with EA (3×75 ml). The combined extracts were washed with brine (100 ml) dried and evaporated and the residue was purified by chromatography using 99:1 EA-Et$_3$N as eluant to give the title compound as an oil (0.855 g).

Analysis Found: C, 79.8; H, 8.9; N, 3.7. C$_{28}$N$_{37}$NO$_2$ requires C, 80.2; H, 8.9; N, 3.3%.

The following compounds were prepared in a similar manner:
(b) (1α,2β,3β)-(±)-1-[2-(3-Methoxy-2-propenyl)-3-[[4′-methyl(1,1′-biphenyl)-4-yl]methoxy]cyclopentyl]piperidine, from Intermediate 19a and 4-bromethyl-4′-methyl(1,1′-biphenyl)). Purification by chromatography using 99:1 EA-Et₃N as eluant.

Analysis Found: C, 80.1; H, 8.9; N, 3.7. C₂₈H₃₇NO₂ requires: C, 80.2; H, 8.9; N, 3.3%.

(c) [1α,2β,3β(E)]-(±)-1-[2-(3-Methoxy-2-propenyl)-3-[(3-phenyl-2-propenyl)oxy]cyclopentyl]piperidine, from Intermediate 19a and cinnamyl bromide. Purification by chromatography using initially 199:1 EA-Et₃N followed by 197:2:1 EA-methanol-Et₃N as eluant.

Analysis Found: C, 77.8; H, 9.5; N, 4.0. C₂₃H₃₃NO₂ requires C, 77.7; H, 9.4; N, 3.9%.

(d) (1α,2β,3β)-(±)-1-[2-(3-Methoxy-2-propenyl)-3-(Phenylmethoxy)cyclopentyl]piperidine, from Intermediate 19a and benzyl chloride. Purification by chromatography using initially EA followed by 199:1 EA-Et₃N.

Analysis Found: C, 76.5; H, 9.7; N, 4.2. C₂₁H₃₁NO₂ requires C, 76.6; H, 9.5; N, 4.25%.

(e) (1α,2β,3β)-(±)-1-[2-(3-Methoxy-2-propenyl)-3-(2-naphthalenylmethoxy)cyclopentyl]piperidine, from Intermediate 19a and 2-(bromomethyl)naphthylene. Purification by chromatography on Et₃N deactivated silica using EA as eluant.

Analysis Found: C, 78.9; H, 8.6; N, 3.5. C₂₅H₃₃NO₂ requires C, 79.1; H, 8.8; N, 3.7%.

(f) (1α,2β,3β)-(±)-1-[2-(3-Methoxy-2-propenyl)-3-[[4-(2-thienyl)phenyl]methoxy]cyclopentyl]piperidine, from Intermediate 19a and 2-[4-bromomethyl)phenyl]thiophene. Purification by chromatography on Et₃N deactivated silica using EA as eluant.

Analysis Found: C, 73.0; H, 8.2; N, 3.3. C₂₅H₃₃NO₂S requires C, 73.0; H, 8.1; N, 3.4%.

(g) (1α,2β,3β)-(±)-1-[3-[3-[(1,1′-Biphenyl)-4-yl]propoxy]-2-(3-methoxy-2-propenyl)cyclopentyl]piperidine, from Intermediate 19a and 3-[(1,1′-biphenyl)-4-yl]propanol, 4-methylbenzenesulphonate. Purification by chromatography on Et₃N deactivated silica eluting with EA.

Analysis Found: C, 80.0; H, 9.0; N, 3.2. C₂₉H₃₉NO₂ requires C, 80.3; H, 9.1; N, 3.2%.

(h) (1α,2β,3β)-(±)-1-[2-(3-Methoxy-2-propenyl)-3-[(5-phenyl-3-thienyl)methoxy]cyclopentyl]piperidine, from Intermediate 19a and 4-(bromomethyl)-2-phenylthiophene. Purification by chromatography on Et₃N deactivated silica eluting with EA.

Analysis Found: C, 72.4; H, 8.0; N, 3.3. C₂₅H₃₃NO₂ requires C, 72.95; H, 8.1; N, 3.4%.

(i) (1α,2β,3β)-(±)-1-[3-[[(1,1′-Biphenyl-4-yl]methoxy]-2-(3-methoxy-2-propenyl)cyclopentyl]-4-methylpiperidine, from Intermediate 19c and 4-bromomethyl(1,1′-biphenyl). Purification by chromatography using 1:1 ER-PE as eluant.

Analysis Found: C, 79.9; H, 8.7; N, 3.7. C₂₈H₃₇NO₂ requires C, 80.15; H, 8.9; N, 3.3%.

(j) (1α,2β,3β)-(±)-1-[3-[[(1,1′-Biphenyl)-4-yl]methoxy]-2-(3-methoxy-2-propenyl)cyclopentyl]-4-methylpiperazine, from Intermediate 19d and 4-bromomethyl (1,1′-biphenyl). Purification by chromatography using initially 50:1 EA-Et₃N followed by 85:15:1 EA-methanol-Et₃N as eluant.

I.r. (Neat) 1653 cm⁻¹.

(k) (1α,2β,3β)-(±)-4-[3-[[(1,1′-Biphenyl)-4-yl]methoxy]-2-(3-methoxy-2-propenyl)cyclopentyl]thiomorpholine 1,1-dioxide, m.p. 92°–93° from Intermediate 19e and 4-bromomethyl(1,1′-biphenyl). Purification by chromatography using ER as eluant.

(l) (1α,2β,3β)-(±)-[3-[[(1,1′-Biphenyl)-4-yl]methoxy]-2-(3-methoxy-2-propenyl)cyclopentyl]pyrrolidine, from Intermediate 19f and 4-bromomethyl(1,1′-biphenyl). Purification by chromatography using 94:5:1 EA-methanol-Et₃N as eluant.

Analysis Found: C, 80.0; H, 8.5; N, 3.8. C₂₆H₃₃NO₂ requires C, 79.75; H, 8.5; N, 3.6%.

(m) (1α,2β,3β)-(±)-1-[3-[[(1,1′-Biphenyl)-4-yl]methoxy]-2-(3-methoxy-2-propenyl)cyclopentyl]hexahydro-1H-azepine, from Intermediate 19g and 4-bromomethyl(1,1′-biphenyl). Purification by chromatography on Et₃N deactivated silica eluting initially with 1:1 CH₂Cl₂-ER then ER.

Analysis Found: C, 79.9; H, 8.7; N, 3.5. C₂₈H₃₇NO₂ requires C, 80.15; H, 8.9; N, 3.3%.

Intermediate 23

(a) (1α,2α,5β)-(±)-2-[[(1,1′-Biphenyl)-4-yl]methoxy]-5-(1-piperidinyl)cyclopentanepropanal A solution of Intermediate 20 (1.3 g) in analar acetone (10 ml) and 5N HCl (3 ml) was stirred at ambient temperature for 5 h. The mixture was adjusted to ca. pH 8 using 5N NaOH (3 ml) and 8% NaHCO₃ solution (20 ml) and extracted with CH₂Cl₂ (3×50 ml). The combined extracts were dried and evaporated to give the title compound (1.18 g) m.p. 65°–68°.

The following compounds were prepared in a similar manner:

(b) [1R-(1α,2α,5β)]-(+)-2-[[(1,1′-Bisphenyl)-4-yl]methoxy]-5-(1-piperidinyl)cyclopentanepropanal, m.p. 88°–92° from Intermediate 19b.

$[\alpha]_D^{24} = +76.1°$ (CHCl₃).

(c) (1α,2α,5β)-(±)-2-[4-(1,1-Dimethylethyl)phenylmethoxy]-5-(1-piperidinyl)cyclopentanepropanal, from Intermediate 21

I.r. (CHBr₃) 1715 cm⁻¹.

(d) (1α,2α,5β)-(±)-2-[[4-(Phenylmethyl)phenyl]methoxy]-5-(1-piperidinyl)cyclopentanepropanal, from Intermediate 22a I.r. (CHBr₃) 2730, 1720 cm⁻¹.

(e) (1α,2α,5β)-(±)-2-[[4′-Methyl(1,1′-biphenyl)-4-yl]methoxy]-5-(1-piperidinyl)cyclopentanepropanal, from Intermediate 22b I.r. (CHBr₃) 2725, 1715 cm⁻¹.

(f) [1α,2α(E),5β)-(±)-2-[(3-Phenyl-2-propenyl)oxy]-5-(1-piperidinyl)cyclopentanepropanal, from Intermediate 22c I.r. (CHBr₃) 2740, 1722, 970 cm⁻¹.

(g) (1α,2α,5β)-(±)-2-(Phenylmethoxy)-5-(1-piperidinyl)cyclopentanepropanal, from Intermediate 22d I.r. (CHBr₃) 2740, 1720 cm⁻¹.

(h) (1α,2α,5β)-(±)-2-(2-Napthalenylmethoxy)-5-(1-piperidinyl)cyclopentanepropanal, from Intermediate 22e I.r. (CHBr₃) 2720, 1720 cm⁻¹.

(i) (1α,2β,5α)-(±)-2-(1-Piperidinyl)-5-[[4-(2-thienyl)phenyl]methoxy]cyclopentanepropanal, from Intermediate 22f I.r. (CHBr₃) 2720, 1720 cm⁻¹.

(j) (1α,2α,5β)-(±)-2-[3-[(1,1′-Biphenyl)-4-yl]propoxy]-5-(1-piperidinyl)cyclopentanepropanal, from Intermediate 22g I.r. (CHBr₃) 2720, 1720 cm⁻¹.

(k) (1α,2α,5β)-(±)-2-[(5-Phenyl-3-thienyl)methoxy]-5-(1-piperidinyl)cyclpentanepropanal, from Intermediate 22h I.r. (CHBr₃) 2730, 1715 cm⁻¹.

(l) (1α,2α,5β)-(±)-2-[[(1,1'-Biphenyl)-4-yl]methoxy]-5-(4-methyl-1-piperidinyl)cyclopentanepropanal, from Intermediate 22i
I.r. (CHBr₃) 2720, 1720 cm⁻¹.

(m) (1α,2α,5β)-(±)-2-[[(1,1'-Biphenyl)-4-yl]methoxy]-5-(4-methyl-1-piperazinyl)cyclopentanepropanal, from Intermediate 22j
I.r. (CHBr₃) 1720 cm⁻¹.

(n) (1α,2α,5β)-(±)-2-[[(1,1'-Biphenyl)-4-yl]methoxy]-5-(4-thiomorpholinyl)cyclopentanepropanal S,S-dioxide, from Intermediate 22k. I.r. (CHBr₃) 2720, 1720, 1330 cm⁻¹.

(o) (1α,2α,5β)-(±)-2-[[(1,1'-Biphenyl)-4-yl]methoxy]-5-(1-pyrrolidinyl)cyclopentanepropanal, from Intermediate 22l
I.r. (CHBr₃) 2720, 1715 cm⁻¹.

(g) (1α,2α,5β)-(±)-2-[[(1,1'-Biphenyl)-4-yl]methoxy]-5-(hexahydro-1H-azepin-1-yl)cyclopentanepropanal, from Intermediate 22m.
I.r. (CHBr₃) 2720, 1715 cm⁻¹.

Intermediate 24

[1R-[1α(Z),2α,5β]]-(+)-7-[2-[[(1,1'-Biphenyl)-4-yl]methoxy]-5-(1-piperidinyl)cyclopentyl]-4-heptenenitrile 3-Cyanopropyltriphenylphosphonium bromide (2.1 g) was added to a cold (0°), stirred solution of potassium t-butoxide (0.58 g) in dry THF (20 ml) under nitrogen. After 20 min a solution of Intermediate 23b (0.65 g) in THF (10 ml) was added dropwise. After a further 45 min methanol (30 ml) was added and the solvents were removed in vacuo. The residue in pH 6.5 phosphate buffer was extracted with EA (2×50 ml). The combined extracts were dried and evaporated and the residue was purified by chromatography on activity 2 alumina using 3:2 ER-PE as eluant to give the title compound (0.64 g) m.p. 39°–40°.
$[\alpha]_D^{23.6} = +87.2°$ (CHCl₃).

Intermediate 25

[1R-[1α(Z),2α,5β]]-(+)-(Triphenylmethyl) 7-[2-[[(1,1'-Biphenyl)-4-yl]methoxy]-5-(1-piperidinyl)cyclopentyl]-4-heptenoate A mixture of trityl chloride (0.18 g), the product of Example 3, base (0.31 g) and Et₃N (2.02 g) in CH₂Cl₂ (5 ml) was stirred at ambient temperature for 66 h. The mixture was diluted with pH 6.5 phosphate buffer (40 ml) and extracted with ER (3×30 ml). The combined extracts were dried and evaporated and the residue was purified by chromatography on Et₃N deactivated silica eluting with 2:3 ER-PE to give the title compound as an oil (0.31 g). I.r. (CHBr₃) 1735 cm⁻¹.
$[\alpha]_D^{22.6} = +52°$ (CHCl₃).

Intermediate 26

[1R-[1α(Z),2α,5β]]-(+)-(Diphenylmethyl) 7-[2-[[(1,1'-Biphenyl)-4-yl]methoxy]-5-(1-piperidinyl)cyclopentyl]-4-heptenoate A mixture of the compound of Example 3, base (0.31 g) and diphenyl-diazomethane (0.39 g) in benzene (10 ml) was stirred at ambient temperature for 22 h then heated to 50° for 9 h. The solvent was removed in vacuo and the residue was purified by chromatography on Et₃N deactivated silica eluting with 2:1 PE-ER to give the title compound as an oil (0.36 g). I.r. (CHBr₃) 1730 cm⁻¹.
$[\alpha]_D^{23.7} = +56°$ (CHCl₃).

Intermediate 27

[1R-[1α(Z),2α,5β]]-(+)-[(1,1-Dimethylethyl)diphenylsilyl]7-[2-[[(1,1'-Biphenyl)-4-yl]methoxy]-5-(1-piperidinyl)cyclopentyl]-4-heptenoate A mixture of the compound of Example 3, base, (0.31 g), Et₃N (121 mg) and (1,1-Dimethylethyl)diphenylsilylchloride (0.275 g) in CH₂Cl₂ (5 ml) was stirred at ambient temperature for 21 h. The mixture was diluted with pH 6.5 phosphate buffer (30 ml) and extracted with ER (3×35 ml). The combined extracts were washed with saturated NaCl solution, dried and evaporated to give the title compound as an oil.
I.r. (CHBr₃) 1720 cm⁻¹.

Intermediate 28

[1R-[1α(Z),2α,5β]]-(+)-7-[2-[[(1,1'-Biphenyl)-4-yl]methoxy]-5-(1-piperidinyl)cyclopentyl]-4-heptynoic acid, hydrochloride A solution of bromine in CH₂Cl₂ (5% v/v; 8.1 ml) was added over 0.5 h to a cooled (0°) stirred solution of the compound of Example 1a (3.657 g) in CH₂Cl₂ (15 ml). After a further 1 h the mixture was washed with 7% Na₂S₂O₃ solution (2×10 ml) and 8% NaHCO₃ solution (2×10 ml), dried and treated with an excess of ethereal HCl. The solvents were removed in vacuo to give a solid (4.75 g).

The solid (5.5 g) in dry DMSO (120 ml) was cooled (0°), and stirred under nitrogen while potassium t-butoxide (12.32 g) was added. The mixture was stirred at ambient temperature for 19 h then diluted with water (30 ml), 5N HCl (20 ml) and pH 6.5 phosphate buffer (100 ml) and extracted with EA (3×80 ml). The combined extracts were washed with brine (2×50 ml) dried and evaporated and the residue was purified by chromatography (twice), using 17:2:1 CH₂Cl₂-ethanol-Et₃N, then 13:6:1 ER-ethanol-Et₃N as eluant. The product in pH 6.5 phosphate buffer (40 ml) was extracted with CH₂Cl₂ (2×25 ml) and the combined, dried extracts were treated with an excess of ethereal HCl. The solvents were removed in vacuo and the residue was co-evaporated with ER to give the title compound as a foam (1.17 g).
T.l.c. 17:2:1 CH₂Cl₂-ethanol-Et₃N Rf 0.42.
$[\alpha]_D^{23.6} = +90°$ (CHCl₃).

EXAMPLE 1

(a) [1R-[1α(Z),2α,5β]]-(+)-Methyl 7-[2-[[(1,1'-Biphenyl)-4-yl]methoxy]-5-(1-piperidinyl)cyclopentyl]-4-heptenoate A solution of tri-n-butyltin hydride (18.72 g) and AIBN (847 mg) in toluene (55 ml) was added over 10 min to a solution of Intermediate 10a (25.8 g) in toluene (140 ml) at 100° under nitrogen. The mixture was heated under reflux for 15 min., cooled and evaporated in vacuo. The residue was purified by chromatography (twice), firstly using 19:1 PE-ER as eluant and secondly using gradient elution from 40:15:1 PE-ER-Et₃N up to 25:25:1 PE-ER-Et₃N to give the title compound as an oil (13.31 g). I.r. (CHBr₃) 1730 cm⁻¹.

Analysis Found: C, 78.1; H, 8.5; N, 2.9. C₃₁H₄₁NO₃ requires C, 78.3; H, 8.7; N, 2.95%.
$[\alpha]_D^{23} = +75.8°$ (CHCl₃).

The following compounds were prepared in a similar manner:

(b) [1R-[1α(Z),2α,5β]]-(+)-Methyl 7-[2-[[(1,1'-Biphenyl)-4-yl]methoxy]-5-(4-morpholinyl)cyclopentyl]-4-heptenoate, from Intermediate 10c. Purification by chromatography initially on activity 2 alumina eluting with 3:2 ER-PE then on silica eluting with ER. I.r. (CHBr$_3$) 1728 cm$^{-1}$ Analysis Found: C, 74.9; H, 8.5; N, 3.3. C$_{30}$H$_{39}$NO$_4$ requires C, 75.4; H, 8.2; N, 2.9.

[α]$_D^{21.2}$ = +80.4° (CHCl$_3$).

(c) [1R-[1α(Z),2α,5β]]-(+)-Methyl 7-[2-[[4'-Methoxy(1,1'-biphenyl)-4-yl]methoxy]-5-(1-piperidinyl)cyclopentyl]-4-heptenoate, from Intermediate 10d. Purification by chromatography using initially 1:1 PE:ER then 49:49:2 PE-ER-Et$_3$N as eluant. I.r. (CHBr$_3$) 1730 cm$^{-1}$.

Analysis Found: C, 75.9; H, 8.6; N, 3.2. C$_{32}$H$_{43}$NO$_4$ requires C, 76.0; H, 8.6; N, 2.8%.

[α]$_D^{25}$ = +68° (CHCl$_3$).

EXAMPLE 2

(a) [1α(Z),2α,5β]-(±)-Methyl 7-[2-[[(1,1'-Biphenyl)-4-yl]methoxy]-5-(1-piperidinyl)cyclopentyl]-4-heptenoate (3-Carboxypropyl)triphenylphosphonium bromide (3.9 g) was added to a stirred solution of potassium t-butoxide (1.95 g) in dry THF (30 ml). After 0.5 h a solution of Intermediate 23a (1.1 g) in dry THF (5 ml) was added and the mixture stirred for 2 h at ambient temperature. Methanol (10 ml) was added and the mixture was concentrated in vacuo. The residue, which contained [1α(Z),2α,5β]-(±)-7-[2-[[(1,1'-Biphenyl)-4-yl]methoxy]-5-(1-piperidinyl)cyclopentyl]-4-heptenoic acid, in methanol (30 ml) containing conc. H$_2$SO$_4$ (5 ml) was kept at ambient temperature for 18 h then concentrated in vacuo. The residue was adjusted to pH 8 with 5N NaOH (5 ml) and 8% NaHCO$_3$ solution (200 ml). The mixture was extracted with CH$_2$Cl$_2$ (3×100 ml) and the combined extracts were dried and evaporated. The residue was purified by chromatography using 49:1 ER-Et$_3$N as eluant to give the title compound as an oil (0.64 g). I.r. (CHBr$_3$) 1730 cm$^{-1}$.

Analysis Found: C, 78.25; H, 8.8; N, 2.8. C$_{31}$H$_{41}$NO$_3$ requires C, 78.3; H, 8.7; N, 2.9%.

The following compounds were prepared in a similar manner:

(b) [1α(Z),2α,5β]-(±)-Methyl 7-[2-[4-(1,1-Dimethylethyl)phenylmethoxy]-5-(1-piperidinyl)cyclopentyl]-4-heptenoate, from Intermediate 23c. Purification by chromatography using 80:20:1 EA-PE-Et$_3$N as eluant.

I.r. (CHBr$_3$) 1730 cm$^{-1}$.

Analysis Found: C, 76.5; H, 10.0; N, 3.1. C$_{29}$H$_{45}$NO$_3$ requires C, 76.4; H, 10.0; N, 3.1%.

(c) [1α(Z),2α,5β]-(±)-Methyl 7-[2-[[4-(Phenylmethyl)phenyl]methoxy]-5-(1-piperidinyl)cyclopentyl]-4-heptenoate, from Intermediate 23d. Purification by chromatography on Et$_3$N deactivated silica using ER as eluant. I.r. (CHBr$_3$) 1725 cm$^{-1}$.

Analysis Found: C, 78.7; H, 8.7; N, 3.2. C$_{32}$H$_{43}$NO$_3$ requires C, 78.5; H, 8.9; N, 2.9%.

(d) [1α(Z),2α,5β]-(±)-Methyl 7-[2-[[4'-Methyl(1,1'-biphenyl)-4-yl]methoxy]-5-(1-piperidinyl)cyclopentyl]-4-heptenoate, from Intermediate 23e. Purification by chromatography on Et$_3$N deactivated silica using ER as eluant. I.r. (CHBr$_3$) 1725 cm$^{-1}$.

Analysis Found: C, 78.3; H, 8.6; N, 2.6. C$_{32}$H$_{43}$NO$_3$ requires C, 78.5; H, 8.9; N, 2.9%.

(e) [1α(Z),2α(E),5β]-(±)-Methyl 7-[2-(3-Phenyl-2-propenyl)oxy]5-(1-piperidinyl)cyclopentyl]-4-heptenoate, from Intermediate 23f. Purification by chromatography on Et$_3$N deactivated silica eluting initially with 1:1 CH$_2$Cl$_2$-ER then ER. I.r. (CHBr$_3$), 1730, 970 cm$^{-1}$.

Analysis Found: C, 76.2; H, 9.5; N, 3.4. C$_{27}$H$_{39}$NO$_3$ requires C, 76.2; H, 9.2; N, 3.3%.

(f) [1α(Z),2α,5β]-(±)-Methyl 7-[2-(Phenylmethoxy)-5-(1-piperidinyl)cyclopentyl]-4-heptenoate, from Intermediate 23g. Purification by chromatography on Et$_3$N deactivated silica eluting initially with 1:1 CH$_2$Cl$_2$-ER then ER. I.r. (CHBr$_3$) 1730 cm$^{-1}$.

Analysis Found: C, 75.1; H, 9.7; N, 3.8. C$_{25}$H$_{37}$NO$_3$ requires C, 75.15; H, 9.3; N, 3.5%.

(g) [1α(Z),2α,5β]-(±)-Methyl 7-[2-(2-Naphthalenylmethoxy)-5-(1-piperidinyl)cyclopentyl]-4-heptenoate, from Intermediate 23h. Purification by chromatography on Et$_3$N deactivated silica using ER as eluant. I.r. (CHBr$_3$) 1726 cm$^{-1}$.

Analysis Found: C, 77.4; H, 8.5; N, 2.9. C$_{29}$H$_{39}$NO$_3$ requires C, 77.5; H, 8.7; N, 3.1%.

(h) [1α(Z),2β,5α]-(±)-Methyl 7-[2-(1-Piperidinyl)-5-[[4-(2-thienyl)phenyl]methoxy]cyclopentyl]-4-heptenoate, from Intermediate 23i. Purification by chromatography on Et$_3$N deactivated silica using ER as eluant. I.r. (CHBr$_3$) 1725 cm$^{-1}$.

Analysis Found: C, 72.8; H, 8.2; N, 2.8. C$_{29}$H$_{39}$NO$_3$S requires C, 72.3; H, 8.1; N, 2.9%.

(i) [1α(Z),2α,5β]-(±)-Methyl 7-[2-[3-[(1,1'-Biphenyl)-4-yl]propoxy]-5-(1-piperidinyl)cyclopentyl]-4-heptenoate, from Intermediate 23j. Purification by chromatography on Et$_3$N deactivated silica using ER as eluant. I.r. (CHBr$_3$) 1725 cm$^{-1}$.

Analysis Found: C, 78.5; H, 9.0; N, 2.8. C$_{33}$H$_{45}$NO$_3$ requires C, 78.7; H, 9.0; N, 2.8%.

(j) [1α(Z),2α,5β]-(±)-Methyl 7-[2-[(5-Phenyl-3-thienyl)methoxy]-5-(1-piperidinyl)cyclopentyl]-4-heptenoate, from Intermediate 23k. Purification by chromatography on Et$_3$N deactivated silica eluting with 1:1 CH$_2$Cl$_2$-ER then ER. I.r. (CHBr$_3$) 1730 cm$^{-1}$.

Analysis Found: C, 72.65; H, 8.4; N, 2.9. C$_{29}$H$_{39}$NO$_3$S requires C, 72.3; H, 8.2; N, 2.9%.

(k) [1R-[1α(Z),2α,5β]]-(+)-Methyl 9-[2-[[(1,1'-Biphenyl)-4-yl]methoxy]-5-(1-piperidinyl)cyclopentyl]-6-nonenoate, from Intermediate 23b and (5-carboxypentyl)triphenylphosphonium bromide. Purification by chromatography using 50:1 ER-Et$_3$N as eluant.

I.r. (CHBr$_3$) 1730 cm$^{-1}$.

Analysis Found: C, 78.3; H, 8.6; N, 2.5. C$_{33}$H$_{45}$NO$_3$ requires C, 78.7; H, 9.0; N, 2.8%.

(l) [1α(Z),2α,5β]-(±)-Methyl 7-[2-[[(1,1'-Biphenyl)-4-yl]methoxy]-5-(hexahydro-1H-azepin-1-yl)cyclopentyl]-4-heptenoate, from Intermediate 23p. Purification by chromatography on Et$_3$N deactivated silica eluting initially with CH$_2$Cl$_2$ then with 9:1 CH$_2$Cl$_2$-ER increasing to 2:1 CH$_2$Cl$_2$-ER. I.r. (CHBr$_3$) 1730 cm$^{-1}$.

Analysis Found: C, 78.6; H, 8.9; N, 3.25. C$_{32}$H$_{43}$NO$_3$ requires C, 78.5; H, 8.85; N, 2.9%.

(m) [1α(Z),2α,5β]-(±)-Methyl 7-[2-[[(1,1'-Biphenyl)-4-yl]methoxy]-5-(4-thiomorpholinyl)cyclopentyl]-4-heptenoate, S,S-dioxide, from Intermediate 23n. Purification by chromatography using ER as eluant. T.l.c. ER Rf 0.4

I.r. (CHBr$_3$) 1725 cm$^{-1}$.

(n) [1α(Z),2α,5β]-(±)-Methyl 7-[2-[[(1,1'-Biphenyl)-4-yl]methoxy]-5-(4-methyl-1-piperidinyl)cyclopentyl]-4-heptenoate, from Intermediate 23l. Purification by chromatography using 75:25:1 PE-ER-Et$_3$N as eluant. I.r. (CHBr$_3$) 1730 cm$^{-1}$.

Analysis Found: C, 78.7; H, 8.6; N, 3.2. C$_{32}$H$_{43}$NO$_3$ requires C, 78.5; H, 8.85; N, 2.9%.

(o) [1α(Z),2α,5β]-(±) Methyl 7-[2-[[(1,1'-Biphenyl)-4-yl]methoxy]-5-(1-pyrrolidinyl)cyclopentyl]-4-heptenoate, from Intermediate 23o. Purification by chromatography on Et$_3$N deactivated silica using 2:1 ER-PE as eluant. I.r. (CHBr$_3$) 1730 cm$^{-1}$.

Analysis Found: C, 78.1; H, 8.8; N, 3.4. C$_{30}$H$_{39}$NO$_3$ requires C, 78.05; H, 8.5; N, 3.0%.

(p) [1α(Z),2α,5β]-(±)-Methyl 7-[2-[[(1,1'-Biphenyl)-4-yl]methoxy-5-(4-methyl-1-piperazinyl)cyclopentyl]-4-heptenoate, from Intermediate 23m. Purification by chromatography using ER followed by 90:10:1 ER-methanol-Et$_3$N as eluant. I.r. (CHBr$_3$) 1725 cm$^{-1}$.

Analysis Found: C, 75.6; H, 8.6; N, 5.4. C$_{31}$H$_{42}$N$_2$O$_3$ requires C, 75.9; H, 8.6; N, 5.7%.

EXAMPLE 3

(a) [1R-[1α(Z),2α,5β]]-(+)-7-[2-[[(1,1'-Biphenyl]-4-yl]methoxy]-5-(1-piperidinyl)cyclophentyl]-4-heptenoic acid, hydrobromide 5N NaOH (0.5 ml) was added to the compound of Example 1a (0.4 g) in methanol (2 ml) and the mixture was stirred at ambient temperature for 24 h. Most of the methanol was removed in vacuo and the residue was adjusted to pH 6 using 5N HCl (0.5 ml) and pH 6 phosphate buffer. The mixture was extracted with CH$_2$Cl$_2$ (3×50 ml) and the combined extracts were dried and evaporated. The residue was purified by chromatography using 85:10:5 CH$_2$Cl$_2$-methanol-Et$_3$N as eluant to give an oil. A solution of the oil in CH$_2$Cl$_2$ (20 ml) was washed with pH 6 phosphate buffer (10 ml) dried, and evaporated. The residue in CH$_2$Cl$_2$ (2 ml) was treated with an excess of ethereal hydrogen bromide. The resulting solid was washed with ER and dried to give the title compound (0.275 g)

m.p. 134°–136° [α]$_D^{23.5}$=+69° (CHCl$_3$).

Analysis Found: C, 66.3; H, 7.4; N, 2.6. C$_{30}$H$_{39}$NO$_3$.HBr requires C, 66.4; H, 7.4; N, 2.6%.

(b) [1R-[1α(Z),2α,5β]]-(+)-7-[2-[[(1,1'-Biphenyl)-4-yl]methoxy]-5-(1-piperidinyl)cyclophentyl]-4-heptenoic acid, hydrochloride

Method A

5N NaOH (25 ml) was added to the compound of Example 1a (20.1 g) in methanol (130 ml) and the mixture was stirred vigorously overnight. The mixture was neutralised with 5N HCl (25 ml) and pH 6.5 phosphate buffer (25 ml) then concentrated in vacuo.

The solution was extracted with CH$_2$Cl$_2$ (3×125 ml) and the combined organic extracts were dried and evaporated in vacuo to give a foam, which was dissolved in CH$_2$Cl$_2$ (80 ml), treated with excess ethereal HCl (2M, 40 ml), and evaporated in vacuo followed by co-evaporation with dry ER (50 ml). The oily residue was triturated with dry ER (4×100 ml) causing crystallisation. The mixture was filtered and dried in vacuo to afford the title compound (20.47 g) m.p. 144°–146°.

T.l.c. 17:2:1 CH$_2$Cl$_2$-Ethanol-Et$_3$N Rf 0.18.

[α]$_D^{19}$=+79.9° (CHCl$_3$).

Method B (3-Carboxypropyl)triphenylphosphonium bromide (1.44 g) was added to a stirred solution of potassium t-butoxide (0.735 g) in dry THF (25 ml). After 2 h a solution of Intermediate 23b (0.43 g) in dry THF (10 ml) was added and the mixture stirred for 2 h at ambient temperature. Water (2 ml) was added and the solvents removed in vacuo. The residue in water (100 ml) was extracted with ER (2×60 ml, discarded), neutralised with conc. HCl and pH 6.5 phosphate buffer and extracted with EA (3×60 ml). The EA extracts were dried and evaporated and the residue in CH$_2$Cl$_2$ (4 ml) was treated with an excess of ethereal HCl. The solvents were removed in vacuo and the residue was triturated with ER until solid (0.29 g). A portion was crystallised from CH$_2$Cl$_2$-IPA to give the title compound m.p. 143°–146°.

T.l.c. Identical mixed spot with the product of Method A.

Method C

A solution of the compound of Example 6 (0.26 g) in ethanol (10 ml) and 2N NaOH (5 ml) was heated under reflux for 20 h. The cooled solution was concentrated in vacuo and extracted with EA (2×5 ml., discarded). The aqueous layer was neutralised with 2N HCl (5 ml) and pH 6.5 phosphate buffer (15 ml) and extracted with CH$_2$Cl$_2$ (2×60 ml). The combined organic layers were dried and treated with an excess of ethereal HCl. The solvents were removed in vacuo and the residue triturated with ER to give the title compound (0.23 g) m.p. 144°–146°.

T.l.c. Identical mixed spot with the product of Method A.

Method D

A stirred suspension of the compound of Example 7 (0.26 g) in acetone was treated with Jones reagent (2.67M, 0.5 ml) at 0° and the mixture was stirred at 0° for 2 h. Propan-2-ol (3 ml) was added at 0° and 0.5 h later the mixture was diluted with pH 6.5 phosphate buffer (40 ml) and extracted with EA (3×13 ml). The combined extracts were dried and evaporated and the residue was purified by chromatography using 17:2:1 CH$_2$Cl$_2$-ethanol-Et$_3$N as eluant. The product in pH 6.5 phosphate buffer (10 ml) was extracted with CH$_2$Cl$_2$ (3×5 ml). The combined extracts were washed with 2N HCl (6 ml), dried and evaporated and the residue was triturated with ER until solid. The solid was crystallised from CH$_2$Cl$_2$-IPA to give the title compound (36 mg) m.p. 144.5°–146.5°.

T.l.c. Identical mixed spot with the product of Method A.

Method E

A stirred solution of the compound of Example 8 (115 mg) in acetone (4 ml) at 0° was treated with Jones reagent (0.5M, 1.1 ml) and the mixture was stirred at 0° for 1.5 h. Propan-2-ol (0.5 ml) was added and 1 h later the solution was concentrated in vacuo, diluted with pH 6.5 phosphate buffer and extracted with EA (3×7 ml). The combined extracts were dried and evaporated and the residue in CH$_2$Cl$_2$ (3 ml) was treated with an excess of ethereal HCl. The solvents were removed in vacuo to give a solid (56 mg). A portion was crystallised from CH$_2$Cl$_2$-IPA to give the title compound m.p. 142°–145°.

T.l.c. Identical mixed spot with the product of Method A.

Method F

A solution of Intermediate 24 (0.41 g) in 1:1 methanol-ethanol (20 ml) and 5N NaOH (5 ml) was heated under reflux for 5.5 h. The cooled solution was concentrated in vacuo, diluted with water and acidified with conc. hydrochloric acid. The solution was extracted with CH$_2$Cl$_2$ (3×40 ml) and the dried solvents were evaporated. The residue was triturated with ER until solid and the solid was crystallised from CH$_2$Cl$_2$-IPA to give the title compound (0.145 g) m.p. 142°–145°.

T.l.c. Identical mixed spot with the product of Method A.

Method G

A solution of Intermediate 4 (0.375 g) and thiocarbonyldiimidazole (0.315 g) in THF (5 ml) was stirred at ambient temperature for 17 h. Water (4 ml) was added, the mixture was stirred for a further 0.5 h then concentrated in vacuo. The residue was diluted with water (10 ml), extracted with CH$_2$Cl$_2$ (2×10 ml) and the combined extracts were dried and evaporated. The residue in toluene (10 ml) was maintained at 95° under nitrogen whilst a solution of tri-n-butyltin hydride (0.35 ml) and AIBN (35 mg) in toluene (4 ml) was added over 10 min. After a further 15 min at 100° the solution was cooled, evaporated and the residue in acetonitrile (35 ml) was extracted with PE (2×20 ml). The extracts were washed with 2N HCl (2×15 ml) and the aqueous layers were extracted with CH$_2$Cl$_2$ (2×15 ml). The CH$_2$Cl$_2$ extracts were washed with pH 6.5 phosphate buffer, dried and evaporated and the residue was purified by chromatography (twice) firstly using 17:2:1 CHCl$_3$-ethanol-Et$_3$N as eluant and secondly using 25:2:1 CHCl$_3$-ethanol-Et$_3$N as eluant. The product in CH$_2$Cl$_2$ (8 ml) was washed with pH 6.5 phosphate buffer, dried and treated with an excess of ethereal HCl. The solvents were removed in vacuo and the residue was triturated with ER until solid. The solid was crystallised from CH$_2$Cl$_2$-IPA to give the title compound (42 mg) m.p. 142°–145°.

T.l.c. Identical mixed spot with the product of Method A.

Method H

A mixture of Intermediate 25 (0.26 g), acetone (5 ml) and 2N HCl (4 ml) was stirred at ambient temperature for 4 h. The mixture was concentrated in vacuo and the residue was diluted with 2N HCl (5 ml) and extracted with ER (20 ml., discarded). The aqueous layer was extracted with CH$_2$Cl$_2$ (6×10 ml) and the combined extracts were dried and evaporated. The residue was triturated with ER to give the title compound as a solid (0.112 g). A portion was crystallised from CH$_2$Cl$_2$-IPA m.p. 141°–144°.

T.l.c. Identical mixed spot with the product of Method A.

Method I

Intermediate 26 was converted into the title compound following the procedure described for Method H. m.p. 140°–144°.

T.l.c. Identical mixed spot with the product of Method A.

Method J

Intermediate 27 was converted into the title compound following the procedure described for Method H. m.p. 145°–147°.

T.l.c. Identical mixed spot with the product of Method A.

EXAMPLE 4

(a) [1R-[1α(Z),2α,5β]]-(+)-7-[2-[[4'-Methoxy(1,1'-biphenyl)-4-yl]methoxy]-5-(1-piperidinyl)cyclopentyl]-4-heptenoic acid, hydrochloride A mixture of the compound of Example 1c (1.15 g), methanol (10 ml) and 5N NaOH (2 ml) was vigorously stirred at ambient temperature for 5 h. The mixture was concentrated in vacuo, neutralised with 5N HCl (2 ml) and pH 6.5 phosphate buffer (10 ml) and extracted with CH$_2$Cl$_2$ (3×10 ml). The combined extracts were dried and evaporated and the residue in CH$_2$Cl$_2$ (4 ml) was treated with an excess of ethereal HCl. The solvents were removed in vacuo and the residue was triturated with ER until solid. Recrystallisation from CH$_2$Cl$_2$-IPA gave the title compound (0.83 g) m.p. 127.5°–131°.

Analysis Found: C, 70.4; H, 7.8; N, 2.75. C$_{31}$H$_{41}$NO$_4$.HCl requires C, 70.5; H, 8.0; N, 2.6%.

[α]$_D^{22}$ = +79.7° (CHCl$_3$).

The following compounds were prepared in a similar manner:

(b) [1R-[1α(Z),2α,5β]]-(+)-7-[2-[[(1,1'-Biphenyl)-4-yl]methoxy]-5-(4-morpholinyl)cyclopentyl]-4-heptenoic acid, hydrochloride, m.p. 138°–139° from the compound of Example 1b.

Analysis Found: C, 69.2; H, 7.7; N, 2.7. C$_{29}$H$_{37}$NO$_4$.HCl requires C, 69.65; H, 7.7; N, 2.8%.

[α]$_D^{22}$ = +65.5° (CHCl$_3$).

(c) [1α(Z),2α,5β]-(±)-7-[2-[[(1,1'-Biphenyl)-4-yl]methoxy]-5-(1-piperidinyl)cyclopentyl]-4-heptenoic acid, hydrobromide, m.p. 110°–119° from the compound of Example 2a. Initial purification by chromatography using 17:2:1 CH$_2$Cl$_2$-ethanol-Et$_3$N as eluant.

I.r. (CHBr$_3$) 3480, 3300–2400, 1720 cm$^{-1}$.

(d) [1α(Z),2α,5β]-(±)-7-[2-[4-(1,1-Dimethylethyl)-phenylmethoxy]-5-(1-piperidinyl)cyclopentyl]-4-heptenoic acid, hydrochloride, m.p. 108°–110° from the compound of Example 2b.

Analysis Found: C, 70.2; H, 9.2; N, 2.7. C$_{28}$H$_{43}$NO$_3$.HCl requires C, 70.3; H, 9.3; N, 2.9%.

(e) [1α(Z),2α,5β]-(±)-7-[2-[4-(Phenylmethyl)phenylmethoxy]-5-(1-piperidinyl)cyclopentyl]-4-heptenoic acid, hydrochloride, m.p. 111°–112° from the compound of Example 2c. Purification by crystallisation from methanol-EA.

Analysis Found: C, 72.3; H, 8.2; N, 2.6. C$_{31}$H$_{41}$NO$_3$.HCl requires C, 72.7; H, 8.3; N, 2.7%.

(f) [1α(Z),2α,5β]-(±)-7-[2-[(4'-Methyl(1,1'-biphenyl)-4-yl]methoxy]-5-(1-piperidinyl)cyclopentyl]-4-heptenoic acid, hydrochloride, m.p. 133°–134° from the compound of Example 2d. Purification by crystallisation from methanol-EA.

Analysis Found: C, 72.8; H, 8.2; N, 2.6. C$_{31}$H$_{41}$NO$_3$.HCl requires C, 72.7; H, 8.3; N, 2.7%.

(g) [1α(Z),2α(E),5β]-(±)-7-[2-[(3-Phenyl-2-propenyl)oxy]-5-(1-piperidinyl)cyclopentyl]-4-heptenoic acid, hydrochloride, m.p. 123°–125° from the compound of Example 2e.

I.r. (CHBr$_3$) 2700, 2250, 1720 cm$^{-1}$.

(h) [1α(Z),2α,5β]-(±)-7-[2-(Phenylmethoxy)-5-(1-piperidinyl)cyclopentyl]-4-heptenoic acid, from the compound of Example 2f.

T.l.c. 25:15:8:2 EA-iPrOH-H$_2$O-NH$_4$OH Rf 0.3

I.r. (Film) 3200–1900, 1710, 1600–1550 cm$^{-1}$.

(i) [1α(Z),2α,5β]-(±)-7-[2-(2-Naphthalenylmethoxy)-5-(1-piperidinyl)cyclopentyl]-4-heptenoic acid, hydrochloride, m.p. 154° from the compound of Example 2g. Purification by crystallisation from CH$_2$Cl$_2$-IPA.
Analysis Found: C, 70.9; H, 8.1; N, 2.8. C$_{28}$H$_{37}$NO$_3$.HCl requires C, 71.2; H, 8.1; N, 3.0%.

(j) [1α(Z),2β,5α]-(±)-7-[2-(1-Piperidinyl)-5-[[4-(2-thienyl)phenyl]methoxy[cyclopentyl]-4-heptenoic acid, from the compound of Example 2h.
T.l.c. 25:15:8:2 EA-iPrOH-H$_2$O-NH$_4$OH Rf 0.49.
I.R. (CHBr$_3$) 1720, 1705, 1596 cm$^{-1}$.

(k) [1α(Z),2α,5β]-(±)-7-[2-[3-[(1,1'-Biphenyl)-4-yl]propoxy]-5-(1-piperidinyl)cyclopentyl]-4-heptenoic acid, from the compound of Example 2i.
T.l.c. 25:15:8:2 EA-iPrOH-H$_2$O-NH$_4$OH Rf 0.55.
I.r. (CHBr$_3$) 3100-2200, 1705, 1598 cm$^{-1}$.

(l) [1α(Z),2α,5β]-(±)-7-[2-[(5-Phenyl-3-thienyl)methoxy-5-(1-piperidinyl)cyclopentyl]-4-heptenoic acid, hydrochloride, m.p. 120°-123° from the compound of Example 2j.
I.r. (CHBr$_3$) 3480, 1716 cm$^{-1}$.

(m) [1R-[1α(Z),2α,5β]]-(+)-9-[2-[[(1,1'-Biphenyl)-4-yl]methoxy]-5-(1-piperidinyl)cyclopentyl]-6-nonenoic acid, hydrochloride, m.p. 99.5°-101° from the compound of Example 2k. Purification by crystallisation from CH$_2$Cl$_2$-IPA.
Analysis Found: C, 72.85; H, 8.2; N, 2.5. C$_{32}$H$_{43}$NO$_3$.HCl requires C, 73.05; H, 8.4; N, 2.7%.
$[α]_D^{24} = +80.8°$ (CHCl$_3$)

(n) [1R-[1α(E),2α,5β]]-(+)-7-[2-[[(1,1'-Biphenyl)-4-yl]methoxy]-5-(1-piperidinyl)cyclopentyl]-4-heptenoic acid, hydrochloride, m.p. 103.5°-107° from the compound of Example 5.
Analysis Found: C, 72.1; H, 7.75; N, 2.8. C$_{30}$H$_{39}$NO$_3$ requires C, 72.3; H, 8.1; N, 2.8%.
$[α]_D^{22} = +71.3°$ (CHCl$_3$)

(o) [1α(Z),2α,5β]-(±)-7-[2-[[(1,1'-Biphenyl)-4-yl]methoxy]-5-(hexahydro-1H-azepin-1-yl)cyclopentyl]-4-heptenoic acid, from the compound of Example 2l.
T.l.c. 25:15:8:2 EA-iPrOH-H$_2$O-NH$_4$OH Rf 0.36.
I.r. (CHBr$_3$) 1700, 1595 cm$^{-1}$.

(p) [1α(Z),2α,5β]-(±)-7-[2-[[(1,1'-Biphenyl)-4-yl]methoxy]-5-(4-thiomorpholinyl)cyclopentyl]-4-heptenoic acid S,S-dioxide, hydrochloride, m.p. 110°-115° from the compound of Example 2m.
Analysis Found: C, 63.1; H, 6.8; N, 2.4. C$_{29}$H$_{37}$NO$_5$S.HCl requires C, 63.5; H, 7.0; N, 2.6%.

(q) [1α(Z),2α,5β]-(±)-7-[2-[[(1,1'-Biphenyl)-4-yl]methoxy]-5-(4-methyl-1-piperidinyl)cyclopentyl]-4-heptenoic acid, hydrochloride, from the compound of Example 2n. Trituration with PE gave the title compound as an amorphous solid.
T.l.c. 25:15:8:2 EA-iPrOH-H$_2$O-NH$_4$OH Rf 0.52.
I.r. (CHBr$_3$) 3500-2200, 1715 cm$^{-1}$.

(r) [1α(Z),2α,5β]-(±)-7-[2-[[(1,1'-Biphenyl)-4-yl]methoxy]-5-(1-pyrrolidinyl)cyclopentyl]-4-heptenoic acid, from the compound of Example 2o.
T.l.c. 25:15:8:2 EA-$^i$PrOH-H$_2$O-NH$_4$OH Rf 0.37.
I.r. (CHBr$_3$) 2380(br), 1705,1597 cm$^{-1}$.

(s) [1α(Z),2α,5β]-(±)-7-[2-[[(1,1'-Biphenyl)-4-yl]methoxy]-5-(4-methyl-1-piperazinyl)cyclopentyl]-4-heptenoic acid, dihydrochloride, from the compound of Example 2p.
Trituration with ER gave the title compound as a hydroscopic solid.
T.l.c. 25:15:8:2 EA-$^i$PrOH-H$_2$O-NH$_4$OH Rf 0.36.
I.r. (CHBr$_3$) 2300 (br), 1715, 1595 cm$^{-1}$.

EXAMPLE 5

[1R-[1α(E),2α,5β]]-(+)-Methyl 7-[2-[[(1,1'-Biphenyl)-4-yl]methoxy]-5-(1-piperidinyl)cyclopentyl]-4-heptenoate A solution of the compound of Example 1a (0.915 g) and 4-toluenesulphinic acid (0.38 g) in dioxan (100 ml) was heated at reflux temperature under nitrogen for 5 h. The cooled solution was diluted with EA (150 ml), washed with 8% NaHCO$_3$ solution (100 ml) then dried and evaporated. The residue was purified by chromatography on silica (300 g) impregnated with silver nitrate (30 g) using 12:1 followed by 10:1 EA-ethanol as eluant. The product in EA (30 ml) was washed with water (25 ml), dried and evaporated and the residue was purified by chromatography using 49:49:2 PE-ER-Et$_3$N as eluant to give the title compound as a gum (0.38 g).
I.r. (CHBr$_3$) 1730 cm$^{-1}$.
Analysis Found: C, 78.3; H, 8.6; N, 3.1. C$_{31}$H$_{41}$NO$_3$ requires C, 78.3; H, 8.7; N, 2.95%.
$[α]_D^{23} = +62.7°$ (CHCl$_3$).

EXAMPLE 6

[1R-[1α(Z),2α,5β]]-(+)-7-[2-[[(1,1'-Biphenyl)-4-yl]methoxy]-5-(1-piperidinyl)cyclopentyl]-4-heptenamide Isobutylchloroformate (0.9 ml) was added to a cooled (−10°), stirred solution of the compound of Example 3, hydrochloride (1.012 g) and Et$_3$N (1.1 ml) in acetonitrile (15 ml). After 0.5 h liquid ammonia (2 ml) was added and the mixture was stirred at −10° for 1 h and ambient temperature for 0.5 h. The mixture was diluted with 30% NH$_4$Cl solution (50 ml) and extracted with EA (3×30 ml). The combined extracts were dried and evaporated and the residue was purified by chromatography using 50:10:1 ER-methanol-Et$_3$N as eluant to give the title compound (0.755 g) m.p. 87°-90°.
Analysis Found: C, 77.9; H, 8.9; N, 6.1. C$_{30}$H$_{40}$N$_2$O$_2$ requires C, 78.2; H, 8.75; N, 6.1%.
$[α]_D^{21} = +79°$ (CHCl$_3$).

EXAMPLE 7

[1R-[1α(Z),2α,5β]]-(+)-7-[2-[[(1,1'-Biphenyl)-4-yl]methoxy]-5-(1-piperidinyl)cyclopentyl]-4-hepten-1-ol, hydrochloride The compound of Example 1a (1 g) in dry THF (6 ml) was added slowly at ambient temperature to a stirred solution of LiAlH$_4$ (267 mg) in dry THF (30 ml) under nitrogen. After 1 h 9:1 THF-water (15 ml) was added cautiously then the mixture was filtered and the filtrate evaporated in vacuo The oil in ER (4 ml) was treated with an excess of ethereal HCl and the solvents were evaporated in vacuo. The residual gum was triturated with ER to give the title compound (0.915 g) m.p. 127°-132°.
Analysis Found: C, 73.9; H, 8.5; N, 2.9. C$_{30}$H$_{41}$NO$_2$.HCl requires C, 74.4; H, 8.7; N, 2.9%.
$[α]_D^{22.5} = +79°$ (CHCl$_3$).

EXAMPLE 8

[1R-[1α(Z),2α,5β]]-(+)-7-[2-[[(1,1'-Biphenyl)-4-yl]methoxy]-5-(1-piperidinyl)cyclopentyl]-4-heptenal A solution of the compound of Example 7 (0.306 g) in CH$_2$Cl$_2$ (5 ml) was washed with 2N Na$_2$CO$_3$ solution (10 ml). The aqueous layer was extracted with CH$_2$Cl$_2$ (5 ml) and the combined organic layers were dried and evaporated in vacuo to ca. 4 ml. Et$_3$N (0.5 ml) was added to the solution which was then cooled to (−15°). Pyridine-sulphur trioxide complex (0.51 g) in DMSO (4 ml) was added and the mixture was stirred at −15° for 1 h then quenched with 30% NH₄Cl solution (15 ml). The aqueous layer was extracted with CH₂Cl₂ (2×10 ml) and the combined organic layers were dried and evaporated. The residue was purified by chromatography using 60:40:1 then 50:50:1 PE-ER-Et₃N as eluant to give the title compound as an oil (0.164 g).

I.r. (CHBr₃) 2730, 1720 cm$^{-1}$.

Analysis Found: C, 80.9; H, 9.0; N, 3.1. $C_{30}H_{39}NO_2$ requires C, 80.9; H, 8.8; N, 3.1%.

$[\alpha]_D^{22} = +80°$ (CHCl₃).

EXAMPLE 9

[1R-[1α(Z),2α,5β]]-(+)-7-[2-[[(1,1'-Biphenyl)-4-yl]methoxy]-5-[1-piperidinyl)cyclopentyl]-4-heptenoic acid, hydrochloride Lindlar catalyst (5% Pd on CaCO₃ poisoned with lead; (60 mg) in EA (4 ml) was pre-saturated with hydrogen for 0.5 h. Intermediate 28 (80 mg) in EA (4 ml) was added and stirring continued at ambient temperature under hydrogen for 2 h. The presence of the title compound in the reaction mixture was demonstrated by t.l.c. (SiO₂ impregnated with AgNO₃) using 8:1 EA-AcOH. Rf 0.17; Identical mixed spot with the product of Example 3(b) Method A.

The term "active ingredient" as used below refers to a compound of the invention and may be for example a compound according to one of the previous examples, such as [1R-[1α(Z),2α,5β]]-(+)-7-[2-[[(1,1'-biphenyl)-4-yl]methoxy]-5-(1-piperidinyl)cyclopentyl]-4-heptenoic acid.

Pharmaceutical Examples

Tablets

These may be prepared by direct compression or wet granulation. The direct compression method is preferred but may not be suitable in all cases as it is dependent upon the dose level and physical characteristics of the active ingredient.

| Direct Compression | mg/tablet |
| --- | --- |
| A. Active Ingredient | 100.00 |
| Microcrystalline Cellulose B.P.C. | 298.00 |
| Magnesium Stearate | 2.00 |
| Compression Weight | 400.00 mg |

The active ingredient is sieved through a 250 m$^{-6}$ sieve, blended with the excipients and compressed using 10.0 mm punches. Tablets of other strengths may be prepared by altering the compression weight and using punches to suit.

| Wet Granulation | mg/tablet |
| --- | --- |
| B. Active Ingredient | 100.00 |
| Lactose B.P. | 238.00 |
| Starch B.P. | 40.00 |
| Pregelatinised Maize Starch B.P. | 20.00 |
| Magnesium Stearate B.P. | 2.00 |
| Compressed Weight | 400.00 mg |

The active ingredient is sieved through a 250 m$^{-6}$ sieve and blended with the lactose, starch and pre-gelatinised starch. The mixed powders are moistened with purified water, granules are made, dried, screened and blended with the magnesium stereate. The lubricated granules are compressed into tablets as described for the direct compression formula.

The tablets may be film coated with suitable film forming materials, e.g. methyl cellulose or hydroxylpropyl methyl cellulose using standard techniques. Alternatively the tablets may be sugar coated.

| Capsules | mg/capsule |
| --- | --- |
| Active Ingredient | 100.00 |
| *STA-RX 1500 | 99.00 |
| Magnesium Stearate B.P. | 1.00 |
| Fill Weight | 200.00 mg |

*A form of directly compressible starch supplied by Colorcorn Ltd., Orpington, Kent.

The active ingredient is sieved through a 250 m$^{-6}$ sieve and blended with the other materials. The mix is filled into No. 2 hard gelatin capsules using a suitable filling machine. Other doses may be prepared by altering the fill weight and if necessary changing the capsule size to suit.

| Inhalation cartridges | mg/cartridge |
| --- | --- |
| Active Ingredient (micronised) | 3.00 |
| Lactose B.P. to | 25.00 |

The active ingredient is micronised in a fluid energy mill to a fine particle size range prior to blending with normal tabletting grade lactose in a high energy mixer. The powder blend is filled into No. 3 hard gelatin capsules on a suitable encapsulating machine.

The contents of the cartridge are administered using a powder inhaler.

| Metered Dose Pressurised Aerosol | mg/metered dose | Per Can |
| --- | --- | --- |
| Active Ingredient (micronised) | 0.500 | 120 mg |
| Oleic Acid B.P. | 0.050 | 12 mg |
| Trichlorofluoromethane B.P. | 22.25 | 5.34 g |
| Dichlorodifluoromethane B.P. | 60.90 | 14.62 g |

The active ingredient is micronised in a fluid energy mill to a fine particle size range. The oleic acid is mixed with the trichlorofluoromethane at a temperature of 10°-15° C. and the micronised drug is mixed into this solution with a high shear mixer. The suspension is metered into aluminium aerosol cans and suitable metering valves, delivering a metered dose of 85 mg of suspension, are crimped onto the cans and the dichlorodifluoromethane is pressure filled into the cans through the valves.

| Syrup | mg/5 ml dose |
| --- | --- |
| Active Ingredient | 100.00 |
| Buffer | |
| Flavour | |
| Colour | as required |
| Preservative | |
| Thickening Agent | |
| Sweetening Agent | |
| Purified Water to | 5.00 ml |

The active ingredient, buffer, flavour, colour, preservative, thickening agent and sweetening agent are dissolved in some of the water, the solution is adjusted to volume and mixed. The syrup produced is clarified by filtration.

| Injection for Intravenous Administration | |
|---|---|
| Active Ingredient | 50 mg |
| Water for injections B.P. to | 5 ml |

Sodium chloride or any other suitable material may be added to adjust the tonicity of the solution and the pH may be adjusted to that of maximum stability of the active ingredient using dilute acid or alkali or by the addition of suitable buffer salts. The solution is prepared, clarified and filled into appropriate sized ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen.

| Suspensions | mg/5 ml dose |
|---|---|
| Active ingredient | 100.00 |
| Aluminium monostearate | 75.00 |
| Sweetening agent | |
| Flavour | as required |
| Colour | |
| Fractionated coconut oil to | 5.00 ml |

The aluminium monostearate is dispensed in about 90% of the fractionated coconut oil. The resulting suspension is heated to 115° C. while stirring and then cooled. The sweetening agent, flavour and colour are added and the active ingredient is suitably dispersed. The suspension is made up to volume with the remaining fractionated coconut oil and mixed.

We claim:

1. A compound of the formula (1a) or 1(b)

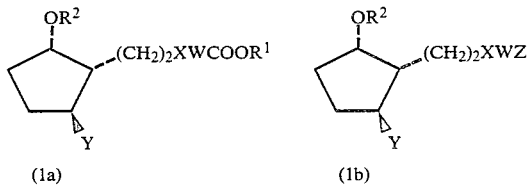

(1a)  (1b)

wherein $R^1$ is a hydrogen atom, or a $C_{1-6}$ alkyl or $C_{7-10}$ aralkyl group;

W is straight or branched $C_{1-7}$ alkylene;

X is cis or trans —CH=CH—;

Y is a saturated heterocyclic amino group (attached to the cyclopentane ring via the nitrogen atom) which is selected from the group consisting of pyrrolidino, piperidino, morpholino, piperazino, thiomorpholino, 1,1-dioxothiomorpholino, homomorpholino and hexamethyleneimino in which the ring carbon atoms can be substituted by methyl, ethyl or butyl and a second nitrogen atom in the ring, if present, can be substituted by methyl, ethyl, butyl, hexyl, benzyl or phenethyl;

$R^2$ is (i) straight or branched $C_{1-5}$ alkyl substituted by (a) phenyl (optionally substituted by $C_{1-6}$ alkyl, $C_{5-7}$ cycloalkyl, phenylalkyl having a $C_{1-3}$ alkyl portion, thienyl, phenyl (optionally substituted by $C_{1-4}$ alkyl, $C_{1-4}$ alkoxy, or phenyl)), (b) thienyl (optionally substituted by $C_{5-7}$ cycloalkyl or phenyl (optionally substituted by $C_{1-3}$ alkyl, $C_{1-3}$ alkoxy or halogen)), or (c) naphthyl (optionally substituted by $C_{1-4}$ alkyl or $C_{1-4}$ alkoxy) or (ii) cinnamyl; and Z is —CH$_2$OH, —CHO or —CONHR$^4$ where $R^4$ is a hydrogen atom or a methyl group; and the physiologically acceptable salts and solvates thereof.

2. Compounds as claimed in claim 1 of the formula (1a).

3. Compounds as claimed in claim 1 in which Y is pyrrolidino, piperidino, hexamethyleneimino or 4-methylpiperidino.

4. Compounds as claimed in claim 1 in which Y is piperidino.

5. Compounds as claimed in claim 1 in which X is cis —CH=CH—.

6. Compounds as claimed in claim 1 in which X is cis —CH=CH— and W is —(CH$_2$)$_2$— or —(CH$_2$)$_4$—.

7. Compounds as claimed in claim 1 in which $R^1$ is a hydrogen atom or a methyl group.

8. Compounds as claimed in claim 1 in which $R^1$ is a hydrogen atom.

9. Compounds as claimed in claim 2 in which:
$R^1$ is a hydrogen atom or a methyl group,
W is —(CH$_2$)$_2$—,
X is cis —CH=CH—, and Y is piperidino, and their physiologically acceptable salts and solvates.

10. Compounds as claimed in claim 1 in which $R^2$ is (i) $C_{1-5}$ alkyl substituted by (a) phenyl or phenyl substituted by phenyl($C_{1-3}$)alkyl, thienyl, phenyl, $C_{1-4}$ alkylphenyl or $C_{1-4}$ alkoxyphenyl, (b) thienyl or phenylthienyl or (c) naphthyl, or (ii) cinnamyl.

11. Compounds as claimed in claim 9 in which $R^2$ is (i) methyl, ethyl or propyl substituted by phenyl (itself substituted by benzyl, thienyl, phenyl, methylphenyl or methoxyphenyl), phenylthienyl or naphthyl, or (ii) cinnamyl.

12. Compounds as claimed in claim 9 in which $R^2$ is benzyl substituted by phenyl, methylphenyl or methoxyphenyl.

13. Compounds as claimed in claim 1 in the form of their 1R-isomers.

14. Compounds as claimed in claim 2, said compounds being:

[1α(Z),2α,5β-(±)-7-[2-[[4'-methoxy(1,1'-biphenyl)-4-yl]methoxy]-5-(1-piperidinyl)cyclopentyl]-4-heptenoic acid, or its 1R isomer;

[1α(Z),2α,5β]-(±)-7-[2-[4-(phenylmethyl)phenylmethoxy]-5-(1-piperidinyl)cyclopentyl]-4-heptenoic acid, or its 1R isomer;

[1α(Z),2α,5β]-(±)-7-[2-[[4'-methyl(1,1'-biphenyl)-4-yl]methoxy]-5-(1-piperidinyl)cyclopentyl]-4-heptenoic acid, or its 1R isomer;

[1α(Z),2β,5α]-(±)-7-[2-(1-piperidinyl)-5-[(4-thien-2-yl)phenylmethoxy]cyclopentyl]-4-heptenoic acid, or its 1R isomer;

[1α(Z),2α,5β]-(±)-7-[2-[3-[(1,1'-biphenyl)-4-yl]propoxy]-5-(1-piperidinyl)cyclopentyl]-4-heptenoic acid, or its 1R isomer;

and their physiologically acceptable salts and solvates.

15. Compounds as claimed in claim 2, said compounds being [1β(Z),2α,5β]-(±)-7-[2-[[(1,1'-biphenyl)-4-yl]methoxy]-5-(1-piperidinyl)cyclopentyl]-4-heptenoic acid and its physiologically acceptable salts and solvates.

16. Compounds as claimed in claim 2, said compounds being [1R-[1α(Z),2α,5β]]-(+)-7-[2-[[(1,1'-biphenyl)-4-yl]methoxy]]-5-(1-piperidinyl)cyclopentyl]-4-heptenoic acid and its physiologically acceptable salts and solvates.

17. The hydrochloride salts of the compounds of claims 15 and 16.

18. A pharmaceutical composition comprising a compound of the formula (1a) or 1(b)

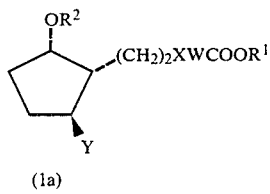

(1a)

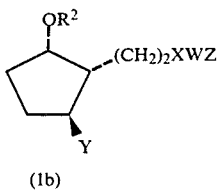

(1b)

wherein
$R^1$ is a hydrogen atom, or a $C_{1-6}$ alkyl or $C_{7-10}$ aralkyl group;
W is straight or branched $C_{1-7}$ alkylene;
X is cis or trans —CH═CH—;
Y is a saturated heterocyclic amino group (attached to the cyclopentane ring via the nigrogen atom) which is selected from the group consisting of pyrrolidino, piperidino, morpholino, piperazino, thiomorpholino, 1,1-dioxothiomorpholino, homomorpholino and hexamethyleneimino in which the ring carbon atoms can be substituted by methyl, ethyl or butyl and a second nitrogen atom in the ring, if present, can be substituted by methyl, ethyl, butyl, hexyl, benzyl or phenethyl;
$R^2$ is (i) straight or branched $C_{1-5}$ alkyl substituted by (a) phenyl (optionally substituted by $C_{1-6}$ alkyl, $C_{5-7}$ cycloalkyl, phenylalkyl having a $C_{1-3}$ alkyl portion, thienyl, phenyl (optionally substituted by $C_{1-4}$ alkyl, $C_{1-4}$ alkoxy, or phenyl)), (b) thienyl (optionally substituted by $C_{5-7}$ cycloalkyl or phenyl (optionally substituted by $C_{1-3}$ alkyl, $C_{1-3}$ alkoxy or halogen)), or (c) naphthyl (optionally substituted by $C_{1-4}$ alkyl or $C_{1-4}$ alkoxy) or (ii) cinnamyl; and Z is —CH$_2$OH, —CHO or —CONHR$^4$ where $R^4$ is a hydrogen atom or a methyl group;
and the physiologically acceptable salts and solvates thereof together with one or more pharmaceutical carriers.

19. A process for the preparation of a compound as claimed in claim 1 which comprises:
(a) in the preparation of a compound of formula (1a), reacting a compound of formula (2)

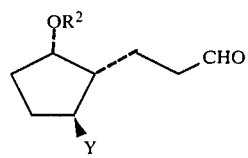

(2)

with a phosphorane of the formula $R_3^5P$=CHWCOOR$^1$ (where $R^5$ is $C_{1-6}$ alkyl or phenyl) or a salt thereof;
(b) in the preparation of a compound of formula (1a) which $R^1$ is a hydrogen atom, hydrolysing a corresponding ester, amide or nitrile;
(c) in the preparation of a compound of formula (1a) in which $R^1$ is $C_{1-6}$ alkyl or $C_{7-10}$ phenalkyl, esterifying the corresponding carboxylic acid;
(d) in the preparation of a compound of formula (1a) dehydroxylating a corresponding alcohol of formula (9)

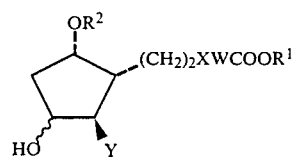

(9)

or a thioester thereof;
(e) in the preparation of a compound of formula (1a), reducing the corresponding compound in which X is an acetylene group;
(f) in the preparation of compounds of formula (1a) in which X is trans —CH═CH—, isomerising the corresponding cis compound;
(g) in the preparation of compounds of formula (1a) in which $R^1$ is hydrogen atom, oxidising a corresponding compound of formula (1b) in which Z is —CH$_2$OH or —CHO;
(h) in the preparation of a compound of formula (1b) in which Z is —CH$_2$OH, reducing the corresponding compound of formula (1a) in which $R^1$ is a methyl group;
(i) in the preparation of a compound of formula (1b) in which Z is —CHO, oxidising the corresponding compound in which Z is —CH$_2$OH;
(j) in the preparation of a compound of formula (1b) in which Z is —CONHR$^4$, amidating the corresponding compound of formula (1a) in which $R^1$ is a hydrogen atom; or
(k) in the preparation of a salt, treating a compound of formula (1a) or (1b) with an acid or a base or converting one salt of a compound of formula (1a) or (1b) into another.

20. A method of inhibiting blood platelet aggregation, bronchoconstriction or vasoconstriction which comprises administering to the patient an effective amount of a compound as claimed in claim 1.

* * * * *